US008147820B2

(12) United States Patent
Hawke et al.

(10) Patent No.: US 8,147,820 B2
(45) Date of Patent: Apr. 3, 2012

(54) **ATTENUATED VACCINE AGAINST FISH PATHOGEN *FRANCISELLA* SP**

(75) Inventors: John Hawke, Baton Rouge, LA (US); Esteban Soto, Basseterre (KN)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 12/881,855

(22) Filed: Sep. 14, 2010

(65) Prior Publication Data

US 2011/0064766 A1 Mar. 17, 2011

Related U.S. Application Data

(60) Provisional application No. 61/242,111, filed on Sep. 14, 2009.

(51) Int. Cl.
*A61K 39/02* (2006.01)

(52) U.S. Cl. ...................................... 424/93.2; 424/93.4

(58) Field of Classification Search ........................ None
See application file for complete search history.

(56) References Cited

U.S. PATENT DOCUMENTS 6,010,705 A 1/2000 Thune et al. ............... 424/234.1

OTHER PUBLICATIONS

Galen et al. (Trends in Microbiol., 9:372-376, 2001).*

Abd, H. et al., "Survival and growth of *Francisella tularensis* in *Acanthamoeba castellanii*," Applied and Environmental Microbiology, vol. 69, pp. 600-606 (2003).

Abril C. et al., "Rapid diagnosis and quantification of *Francisella tularensis* in organs of naturally infected common squirrel monkeys (*Saimiri sciureus*," Vet.Microbiol, vol. 127, pp. 203-208 (2008).

Allen, L.A., "Mechanisms of pathogenesis: evasion of killing by polymorphonuclear leukocytes," Microbes and Infection, vol. 5, pp. 1329-1335 (2003).

Amend, D.F., "Potency testing of fish vaccines," In: Anderson DP, Hennessen H, editors. Fish biologics: serodiagnostics and vaccines. Developments in biological standardization. Basel: Karger; pp. 447-454 (1981).

Anderson, D.P., "Diseases of Fishes," In: S. Zhang, and D. Hua editors. Fish Immunology, China Agriculture Press, Beijing, China, pp. 156-161 (1984).

Baker, C.N. et al., "Antimicrobial susceptibility testing of *Francisella tularensis* with a modified mueller-hinton broth," J Clin Microbiol, vol. 22, No. 2, pp. 212-215 (1985).

Balcazar, J.L. et al., "Quantitative detection of *Aeromonas salmonicida* in fish tissue by real-time PCR using self-quenched, fluorogenic primers," J.Med.Microbiol, vol. 56, pp. 323-328 (2007).

Barker, J.R. et al., "Molecular and genetic basis of pathogenesis in *Francisella tularensis*," Annals of the New York Academy of Sciences, vol. 1105, pp. 138-159 (2007).

Baron, G.S. et al., "MglA and MglB are required for the intramacrophage growth of *Francisella novicida*," Molecular Microbiology, vol. 29, pp. 247-259 (1998).

Birkbeck, T. H. et al., "Identification of *Francisella* sp. from atlantic salmon, *Salmo salar* L., in Chile," Journal of Fish Diseases, vol. 30, pp. 505-507 (2007).

Bode E. et al., "Real-time PCR assay for a unique chromosomal sequence of *Bacillus anthracis*," J.Clin.Microbiol., vol. 42, pp. 5825-5831 (2004).

Brotcke, A. et al., "Identification of MglA-regulated genes reveals novel virulence factors in *Francisella tularensis*. Infection and Immunity," vol. 74, pp. 6642-6655 (2006).

Chapman, F.A., Circular 1051, Department of Fisheries and Aquatic Sciences, Florida Cooperative Extention Service, Institute of Food and Agricultural Sciences, University of Florida (1992).

Clemens, Daniel L. et al., "Uptake and Intracellular Fate of *Francisella tularensis* in Human Macrophages," Ann. N.Y. Acad. Sci., vol. 1105, pp. 160-186 (2007).

de Bruin, O.M. et al., "The *Francisella* pathogenicity island protein IglA localizes to the bacterial cytoplasm and is needed for intracellular growth," BMC Microbiology, vol. 7, pp. 1 (2007).

Dennis, D.T. et al., Tularemia as a biological weapon: medical and public health management. Journal of the American Medical Association, vol. 285, pp. 2763-2773 (2001).

Espy, M.J. et al., "Real-time PCR in clinical microbiology: applications for routine laboratory testing," Clin.Microbiol.Rev., vol. 19, pp. 165-256 (2006).

Gallagher, L.A. et al., "A comprehensive transposon mutant library of *Francisella novicida*, a bioweapon surrogate," Proceedings of the National Academy of Sciences of the United States of America, vol. 104, pp. 1009-1014 (2007).

Getchell, R.G et al., "Quantitative polymerase chain reaction assay for largemouth bass virus," J.Aquat.Anim Health, vol. 19, pp. 226-233 (2007.

Golovliov, I.,V et al., An attenuated strain of the facultative intracellular bacterium *Francisella tularensis* can escape the phagosome of monocytic cells. Infection and Immunity, vol. 71, pp. 5940-5950 (2003).

Golovliov, I. et al., "Identification of proteins of *Francisella tularensis* induced during growth in macrophages and cloning of the gene encoding a prominently induced 23-kilodalton protein," Infection and Immunity, vol. 65, pp. 2183-2189 (1997).

Grabowski, L.D. et al., "Systemic and mucosal antibody response in tilapia, *Oreochromis niloticus* (L.), following immunization with *Flavobacterium columnare*," J Fish Dis., vol. 27, No. 10, pp. 573-581 (2004).

Griffin, M.J. et al., "A real-time polymerase chain reaction assay for the detection of the myxozoan parasite *Henneguya ictaluri* in channel catfish," J. Vet. Diag.Invg., vol. 20: Incomplete (2008).

Hsieh, C.Y. et al., "Enzootics of visceral granulomas associated with *Francisella*-like organism infection in tilapia (*Oreochromis* spp.)," Aquaculture, vol. 254, pp. 129-138 (2006).

(Continued)

*Primary Examiner* — Nita M Minnifield
*Assistant Examiner* — Brian J Gangle
(74) *Attorney, Agent, or Firm* — Bonnie J. Davis; John H. Runnels

(57) ABSTRACT

An attenuated bacteria has been made by an insertion mutation in the iglC gene of *Francisella asiatica*, by allelic exchange. The attenuated strain proved to be an effective vaccine by providing protection against an infection of *F. asiatica* in tilapia, and is believed would at least partially immunize fish from other species of *Francisella*. The vaccine of the attenuated *Francisella asiatica* ΔiglC mutant can also serve as vectors to present antigens from other pathogens to the fish, thereby serving as vaccines against other pathogens as well. In addition, a highly sensitive and specific assay that can be used for the specific identification of *F. asiatica* in fish has been developed.

21 Claims, 10 Drawing Sheets

OTHER PUBLICATIONS

Josupeit, H., "Tilapia Market Report—Apr. 2008. Food and Agriculture Organization of the United Nations (FAO)," On line at: www.fao.org. (2008).

Kamaishi,T. et al., "Identification and pathogenicity of intracellular *Francisella* bacterium in three-line grunt *Parapristipoma trilineatum*," Fish Pathology, vol. 40, pp. 67-71 (2005).

Kang, H.Y. et al., "Immune responses to recombinant pneumococcal PspA antigen delivered by live attenuated *Salmonella enterica* serovar Tymphimurium vaccine," Infection and Immunity, vol. 70, pp. 1739-1749 (2002).

Keim, P. et al., "Molecular epidemiology, evolution, and ecology of *Francisella. Francisella tularensis*," Biology, Pathogenicity, Epidemiology, and Biodefense. Annals of the New York Academy of Sciences, vol. 1105, pp. 30-66 (2007).

Kidd, L. et al., "Evaluation of conventional and real-time PCR assays for detection and differentiation of spotted fever group rickettsia in dog blood," Veterinary Microbiology, vol. 193, pp. 294-303 (2008).

Kocagoz, T. et al., "Rapid determination of rifampin resistance in clinical isolates of *Mycobacterium tuberculosis* by real-time PCR," J.Clin.Microbiol., vol. 43, pp. 6015-6019 (2005).

Lai, X.H. et al., "Expression of IgIC is necessary for intracellular growth and induction of apoptosis in murine macrophages by *Francisella tularensis*," Microbial Pathogenesis, vol. 37, pp. 225-230 (2004.

Lauriano, C.M. et al., "Allelic exchange in *Francisella tularensis* using PCR products," FEMS Microbiology Letters, vol. 229, pp. 195-202 (2003).

Lauriano, C.M. et al., MglA regulates transcription of virulence factors necessary for *Francisella tularensis* intraamoebae and intramacrophage survival, Proceedings of the National Academy of Sciences, vol. 101, pp. 4246-4249 (2004).

Liu, J. et al., Construction of targeted insertion mutations in *Francisella tularensis* subsp. *novicida*, BioTechniques, vol. 43, pp. 487-492 (2007).

Ludu, J.S. et al., "Genetic elements for selection, deletion mutagenesis and complementation in *Francisella* spp.," FEMS Microbiology Letters, vol. 278, pp. 86-93 (2008-a).

Ludu, J.S. et al., "The *Francisella* pathogenicity island protein PdpD is required for full virulence and associates with homologues of the type VI secretion system," Journal of Bacteriology, vol. 190, pp. 4584-4595 (2008-b).

Maier, T.M. et al., "Construction and characterization of a highly efficient *Francisella* shuttle plasmid," Applied and Environmental Microbiology, vol. 70, pp. 7511-7519 (2004.

Mauel, M.J. et al., "A Piscirickettsiosis-like Syndrome in Cultured Nile Tilapia in Latin America with *Francisella* sp. as the Pathogenic Agent," Journal of Aquatic Animal Health, vol. 19, pp. 27-34 (2007).

Mikalsen, J. et al., "*Francisella asiatica* sp. nov. isolated from farmed tilapia (*Oreochromis* sp.) and elevation of *Francisella philomiragia* subsp. *noatunensis* to species rank as *Francisella noatunensis* comb. nov., sp.," International Journal of Systematic and Evolutionary Microbiology, Epub ahead of print on Sep. 25, 2009 (2009).

Mikalsen, J.A. et al., *Francisella philomiragia* subsp *noatunensis* subsp nov., isolated from farmed Atlantic cod (*Gadus morhua* L), International Journal of Systematic and Evolutionary Microbiology, vol. 57, pp. 1960-1965 (2007).

Nano, F.E. et al., "A *Francisella tularensis* pathogenicity island required for intramacrophage growth," Journal of Bacteriology, vol. 186, pp. 6430-6436 (2004).

Nano, F.E. et al., "The *Francisella* pathogenicity island," Annals of the New York Academy of Sciences, vol. 1105, pp. 122-137 (2007).

Neumann, N.F. et al., "Production of a macrophage growth factor(s) by a goldfish macrophage cell line and macrophages derived from goldfish kidney leukocytes," Dev Comp Immunol, vol. 22, No. 4, pp. 417-432 (1998).

Ostland, V.E. et al., "Aquatic *Francisella*-like bacterium associated with mortality of intensively cultured hybrid striped bass *Morone chrysops* x *M. saxatilis*," Diseases of Aquatic Organisms, vol. 72, pp. 135-145 (2006).

Ottem, K.F. et al., "New species in the genus *Francisella* (Gammaproteobacteria; Francisellaceae); *Francisella piscicida* sp. nov. isolated from cod (*Gadus morhua*)," Archives of Microbiology, vol. 188, pp. 547-550 (2007).

Ottem, K.F. et al., "Occurrence of *Francisella piscicida* in farmed and wild Atlantic cod, *Gadus morhua L.*, in Norway," J.Fish Dis., vol. 31, pp. 525-534 (2008).

Panangala, V.S. et al., "TaqMan real-time polymerase chain reaction assay for rapid detection of *Flavobacterium columnare*," Aquaculture Research, vol. 38, pp. 508-517 (2007).

Reed, L.J., "A simple method of estimating fifty percent end points," Am J Hyg, vol. 27, pp. 493-497 (1938).

Roberts, M., "*Salmonella* as carriers of heterologous antigens," pp. 27-58; in O'Hagan (ed.), Novel Delivery Systems for Oral Diseases (1994).

Santic, M. et al., "The *Francisella tularensis* pathogenicity island protein IgIC and its regulator MglA are essential for modulating phagosome biogenesis and subsequent bacterial escape into the cytoplasm," Cell Microbiology, vol. 7, pp. 969-979 (2005).

Secombes, C.J. et al., "Isolation of salmonid macrophages and analysis of their killing activity," In: Stolen, J.S. et al. editors, Techniques in Fish Immunology, vol. 1. New Jersey: SOS Publications; pp. 137-154 (1992).

Shelby, R.A. et al., "Detection of Humoral Response to *Streptococcus iniae* Infection of Nile Tilapia, *Oreochromis niloticus*, by a Monoclonal Antibody-Based ELISA," J Appl Aquac, vol. 12, pp. 23-31 (2002).

Sjostedt, A., "Tularemia: history, epidemiology, pathogen physiology, and clinical manifestations," Annals of the New York Academy of Sciences, vol. 1105, pp. 1-29 (2007).

Soto, E. et al., "Attenuation of the fish pathogen *Francisella* sp. by mutation of the igIC gene," Journal of Aquatic Animal Health, vol. 21, pp. 140-149, epub Oct. 12, 2009 (2009b).

Soto, E. et al., "Development of a Real-time PCR assay for identification and quantification of the fish pathogen *Francisella noatunensis* subsp. *Orientalis*," Diseases of Aquatic Organisms, vol. 89, No. 3, pp. 199-207; epub Apr. 9, 2010 (2010a).

Soto, E. et al., "*Francisella* sp., an emerging pathogen of tilapia, *Oreochromis niloticus* (L.) in Costa Rica," Journal of Fish Disease, vol. 32, pp. 713-722; epub. Jun. 8, 2009. (2009a).

Soto, E. et al., "Interaction of *Francsiella asiatica* with Tilapia (*Oreochromis niloticus*) innate immunity", Infection and Immunity, vol. 78, pp. 2070-2078; epub Feb. 16, 2010 (2010b).

Suzuki K. et al., "Real-time PCR for quantification of viable *Renibacterium salmoninarum* in chum salmon *Oncorhynchus keta*," Dis.Aquat.Organ, vol. 74, pp. 209-223 (2007).

Takahashi, T. et al., Quantitative nested real-time PCR assay for assessing the clinical course of tuberculous meningitis. J.Neurol.Sci., vol. 255, pp. 69-76 (2007).

Tomaso, H. et al., "Real-time PCR using hybridization probes for the rapid and specific identification of *Francisella tularensis* subspecies *tularensis*, " Mol.Cell Probes, vol. 21, pp. 12-16 (2007).

Vonkavaara, M. et al., "*Drosophila melanogaster* as a model for elucidating the pathogenicity of *Francisella tularensis*," Cell Microbiolgy, vol. 10, pp. 1327-1338 (2008).

Birkbeck, T.H. et al., "*Francisella* infections in fish and shellfish," J. of Fish Diseases, vol. 34, pp. 173-187 (2011).

Ottem, K.F. , "Elevation of *Francisella philomiragia* subsp. *noatunensis* Mikalsen et al. (2007) to *Francisella noatunensis* comb. nov. [syn. *Francisella piscicida* Ottem et al. (2008) syn. nov.] and characterization of *Francisella noatunensis* subsp. *orientalis* subsp. nov., two important fish pathogens," J. of Applied Microbiology, vol. 106, pp. 1231-1243 (2009).

* cited by examiner

SEQUENCE LISTING

```
<160> NUMBER OF SEQ ID NOS: 23

<210> SEQ ID NO 1
<211> LENGTH: 30
<212> TYPE: DNA
<213> ORGANISM: Artificial sequence
<220> FEATURE:
<223> OTHER INFORMATION: Synthetic primer

<400> SEQUENCE: 1

aattctcgag tgttggtgct gagcaaattc                                       30


<210> SEQ ID NO 2
<211> LENGTH: 32
<212> TYPE: DNA
<213> ORGANISM: Artificial sequence
<220> FEATURE:
<223> OTHER INFORMATION: Synthetic primer

<400> SEQUENCE: 2

aatttaacta gtcagcacag catacaggca ag                                    32


<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3

tgttggtgct gagcaaattc                                                  20


<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4

cagcacagca tacaggcaag                                                  20


<210> SEQ ID NO 5
```

-continued

<211> LENGTH: 21
<212> TYPE: DNA
<213> ORGANISM: Artificial sequence
<220> FEATURE:
<223> OTHER INFORMATION: Synthetic primer

<400> SEQUENCE: 5
ttttgggttg tcactcatcg t 21

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
cgctataacc ctcttcattt 20

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
gggaagatcg gtagatgcaa 20

<210> SEQ ID NO 8
<211> LENGTH: 22
<212> TYPE: DNA
<213> ORGANISM: Artificial sequence
<220> FEATURE:
<223> OTHER INFORMATION: Synthetic primer

<400> SEQUENCE: 8
cgagtagtgc tctgatttct gg 22

<210> SEQ ID NO 9
<211> LENGTH: 23
<212> TYPE: DNA
<213> ORGANISM: Artificial sequence
<220> FEATURE:
<223> OTHER INFORMATION: Synthetic primer

<400> SEQUENCE: 9
gtcagaagag taaataatgg tgt 23

<210> SEQ ID NO 10
<211> LENGTH: 23
<212> TYPE: DNA
<213> ORGANISM: Artificial sequence
<220> FEATURE:
<223> OTHER INFORMATION: Synthetic primer

<400> SEQUENCE: 10
ggctctatac taatactaaa agc 23

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11

-continued

```
tttagttatt attcgcaccg                                              20


<210> SEQ ID NO 12
<211> LENGTH: 20
<212> TYPE: DNA
<213> ORGANISM: Artificial sequence
<220> FEATURE:
<223> OTHER INFORMATION: Synthetic primer

<400> SEQUENCE: 12

caggaagttt gtcaagatga                                              20


<210> SEQ ID NO 13
<211> LENGTH: 28
<212> TYPE: DNA
<213> ORGANISM: Artificial sequence
<220> FEATURE:
<223> OTHER INFORMATION: Synthetic primer

<400> SEQUENCE: 13

gagtttgaag gaatgaatac tacaatga                                     28


<210> SEQ ID NO 14
<211> LENGTH: 24
<212> TYPE: DNA
<213> ORGANISM: Artificial sequence
<220> FEATURE:
<223> OTHER INFORMATION: Synthetic primer

<400> SEQUENCE: 14

gagccatctt cccaataaat cctt                                         24


<210> SEQ ID NO 15
<211> LENGTH: 21
<212> TYPE: DNA
<213> ORGANISM: Artificial sequence
<220> FEATURE:
<223> OTHER INFORMATION: Synthetic primer

<400> SEQUENCE: 15

gctggagcta ttgcctttct t                                            21


<210> SEQ ID NO 16
<211> LENGTH: 23
<212> TYPE: DNA
<213> ORGANISM: Artificial sequence
<220> FEATURE:
<223> OTHER INFORMATION: Synthetic primer

<400> SEQUENCE: 16

tgctatcctc tatctttgca ggt                                          23


<210> SEQ ID NO 17
<211> LENGTH: 20
<212> TYPE: DNA
<213> ORGANISM: Artificial sequence
<220> FEATURE:
<223> OTHER INFORMATION: Synthetic primer

<400> SEQUENCE: 17

taccagttgg aaacgactgt                                              20


<210> SEQ ID NO 18
<211> LENGTH: 19
<212> TYPE: DNA
<213> ORGANISM: Artificial sequence
<220> FEATURE:
```

<223> OTHER INFORMATION: Synthetic primer

<400> SEQUENCE: 18
cctttttgag tttcgctcc 19

<210> SEQ ID NO 19
<211> LENGTH: 19
<212> TYPE: DNA
<213> ORGANISM: Artificial sequence
<220> FEATURE:
<223> OTHER INFORMATION: Synthetic primer

<400> SEQUENCE: 19
gagtttgatc ctggctcag 19

<210> SEQ ID NO 20
<211> LENGTH: 20
<212> TYPE: DNA
<213> ORGANISM: Artificial sequence
<220> FEATURE:
<223> OTHER INFORMATION: Synthetic primer

<400> SEQUENCE: 20
agaaaggagg tgatccagcc 20

<210> SEQ ID NO 21
<211> LENGTH: 24
<212> TYPE: DNA
<213> ORGANISM: Artificial sequence
<220> FEATURE:
<223> OTHER INFORMATION: Synthetic primer

<400> SEQUENCE: 21
gggcgtatct aaggatggta tgag 24

<210> SEQ ID NO 22
<211> LENGTH: 22
<212> TYPE: DNA
<213> ORGANISM: Artificial sequence
<220> FEATURE:
<223> OTHER INFORMATION: Synthetic primer

<400> SEQUENCE: 22
agcacagcat acaggcaagc ta 22

<210> SEQ ID NO 23
<211> LENGTH: 28
<212> TYPE: DNA
<213> ORGANISM: Artificial sequence
<220> FEATURE:
<223> OTHER INFORMATION: Synthetic primer

<400> SEQUENCE: 23
atctattgat gggctcacaa cttcacaa 28

ATTENUATED VACCINE AGAINST FISH PATHOGEN *FRANCISELLA* SP

The benefit of the Sep. 14, 2009 filing date of U.S. provisional application Ser. No. 61/242,111 is claimed under 35 U.S.C. §119(e).

This invention was made with United States government support under grant no. USDA/CSREES 2009-36100-06293 awarded by the United States Department of Agriculture. The government has certain rights in this invention.

This invention pertains to fish vaccines, particularly to certain attenuated bacterial vaccines against fish pathogens of the genus *Francisella*, especially *Francisella asiatica.*

Immune responses to live vaccines are generally of greater magnitude and of longer duration than those produced by killed or subunit vaccines, particularly against facultative intracellular bacteria. A single dose of a live-attenuated vaccine can provide better protection against later infection by the wild type organism, because the attenuated organism persists and metabolizes within the host, and in some cases may replicate in the host for a time. Live viruses will better trigger cell-mediated immune responses, which play a crucial role in controlling infection due to intracellular pathogens. Injected vaccines are impractical for most large commercial fish cultures due to size of enclosure, number of individual animals, and low value per individual fish. Immersion or oral delivery of killed viruses in fish has yielded inconsistent results. The invasion, persistence, and replication of live attenuated vaccines result in a more effective and inexpensive vaccine. See, U.S. Pat. No. 6,010,705. Currently there are no live attenuated vaccines for fish for the facultative intracellular pathogen *Francisella.*

Members of the genus *Francisella* are small pleomorphic, Gram-negative bacteria, belonging to the gamma group of the class Proteobacteria. Many *Francisella* spp. are facultative intracellular pathogens of macrophages and other various cell types of humans, rabbits, rodents, non-human primates, amoebas, arthropods and fish. Members of the genus *Francisella* are fastidious facultative bacteria that have been found to infect a great variety of animals (including humans), but very little is known regarding the virulence mechanisms and virulence factors of this genus (Barker and Klose 2007; Keim et al. 2007). The different subspecies of *F. tularensis* have been found to exist within macrophages in different vertebrate hosts, arthropods, and in amoebae (Keim and Wagner 2007; Abd et al. 2003; Vonkavaara et al. 2008). Several genes provide the pathogen with properties for survival in the extracellular compartment and also for survival and multiplication inside of potent phagocytes like neutrophils and macrophages (Baron and Nano 1998; Allen 2003; Nano et al. 2004).

*Francisella asiatica* and *Francisella noatunensis* are two recently described members of the genus that cause piscine francisellosis in a wide variety of fish species (Mikalsen et al. 2009). *Francisella asiatica* was also previously called *Francisella noatunensis* subsp. *orientalis. Francisella* spp. are emergent bacterial pathogens that cause acute to chronic disease in warm and cold water cultured and wild fish species. During the past 5 years the bacteria have been implicated as the cause of mortalities in tilapia and other important warm and cold water species cultured in the USA, Taiwan, Costa Rica, Latin America, Hawaii, Norway, Chile, and Japan (three line grunt (*Parapristipoma trilineatum*), Kamaishi et al. 2005; tilapia (*Oreochromis* sp.), Hsieh et al. 2006; hybrid striped bass (*Morone chrysops* x *M. saxatilis*), Ostland et al. 2006; Atlantic salmon (*Salmo salar*), Birckbeck et al. 2007; tilapia, Mauel et al. 2007; Atlantic cod (*Gadus morhua* L.), Mikalsen et al. 2007; cod, Ottem et al. 2007; and tilapia, Soto et al. 2009a). *F. asiatica* has been identified from the tilapia and three line grunt (Mikalsen et al. 2009). Infected fish show non-specific clinical signs such as erratic swimming, anorexia, anemia, exophthalmia and high mortality. Upon gross and microscopic examination, several internal organs (mainly spleen and kidney) are enlarged and contain widespread multifocal white nodules. Histological examination reveals the presence of multifocal granulomatous lesions, with the presence of numerous small, pleomorphic, coccobacilli (Soto et al. 2009a).

*Francisella tularensis* is the most important species belonging to this genus (Dennis et al. 2001; Sjostedt 2007). Besides being an important animal pathogen, *F. tularensis* is a zoonotic agent which has received considerable study as a potential bioterrorism agent. The organism has a high infectivity rate and multiple infectious routes (Keim et al. 2007; Nano and Shmerck 2007). The genetic basis of *F. tularensis* virulence is still poorly understood although several virulence determinants have been identified (Golovliov et al. 2003; Nano et al. 2004; Barker and Klose 2007). Previous studies have described the intracellular localization, survival, replication and escape of *F. tularensis* subspecies, in adherent mouse peritoneal cells, a mouse macrophage-like cell line J774A.1, and a human macrophage cell line THP-1. (Baron and Nano 1998; Golovliov et al 2003; de Bruin et al. 2007). Some of the most interesting genes identified in *F. tularensis* are the genes of the intracellular growth locus (iglA, iglB, iglC, and iglD) present as part of a 30 Kb pathogenicity island (Nano et al. (2004; Barker and Klose 2007). Igl proteins appear to be essential for the ability of *F. tularensis* to survive inside the macrophages and cause disease (Golovliov et al. 1997; Nano et al. 2004; Lai et al. 2004; Lauriano et al. 2004; Santic et al. 2005; Brotcke et al. 2006; de Bruin et al. 2007). Recent data have shown that IglA and IglB are part of a novel *Francisella* Pathogenicity Island (FPI) encoding Type Six Secretion System (T6SS) (Nano and Schmerk, 2007; Ludu et al. 2008-b). Mutations of these four Igl genes in *F. tularensis* have shown decreased pathogenicity of the bacterium both in vivo and in vitro in mammalian and insect tissues and cell lines (Lauriano et al. 2003; Nano et al. 2004; de Bruin et al. 2007; Vonkavaara et al. 2008).

PCR and sequence comparison of the 16S rRNA have made it possible to place the fish *Francisella asiatica* at 97% similarity to *F. tularensis,* 98% similarity to *F. philomiragia*, and 99% to other strains isolated from fish species (Kamaishi et al. 2005; Hsieh et al. 2006; Ostland et al. 2006; Mauel et al. 2007; Mikalsen et al. 2007; Ottem et al. 2007; Soto et al. 2009). *Francisella philomiragia* subsp. *noatunensis* (now called *F. noatunensis*) and *F. piscicida* were recovered from moribund farmed Atlantic cod in Norway (Mikalsen et al. 2007; Ottem et al. 2007) displaying chronic granulomatous disease. Strains from cod in Norway have been characterized by phenotypic and molecular taxonomic methods as closely related members of *F. philomiragia* subsp. *philomiragia* (Mikalsen et al. 2007; Ottem et al. 2007).

Tilapia is one of the most important cultured species in the world. Tilapia is a generic term used to designate a commercially important food group of fish that belong to the family Cichlidae. There are three known genera of tilapia, *Tilapia, Sarotherodon*, and *Oreochromis*. In addition, many hybrids of tilapia are known (Chapman 1992). Worldwide tilapia aquaculture production, mainly Nile tilapia (*Oreochromis niloticus*), has been increasing in exponential proportions during the last decade, to greater than 2.5 million tons in 2005. One such commercial hybrid is red tilapia (*Oreochromis mossambicus* x *O. niloticus*). The main producing countries are China, Ecuador, Egypt, Israel, Indonesia, Singapore, Philippines and Thailand, but Mexico, Costa Rica, Honduras and other Latin-American countries have more than doubled their production in the past five years. The United States of America is the country that imports the highest amount of tilapia, receiving more than 80% of worldwide tilapia exports (Josupeit 2008). As the tilapia aquaculture industry expands, tilapia farms are often challenged with disease outbreaks, which in several cases have caused severe economic losses, due to high mortality events, decreased weight gain, antibiotic and treatment expenses, etc.

Real-time PCR is a well known molecular technique that is currently used in many laboratories for diagnosis of microbial pathogens including the fastidious bacteria *Mycobacterium* spp., *Bacillus anthracis, F. tularensis*, and organisms that are non-culturable on cell free media, the *Rickettsia* spp. and viruses (Bode et al. 2004; Kocagoz et al. 2005; Kidd et al. 2008; Tomaso et al. 2007; Abril et al. 2008; Takahashi et al. 2007). In recent years, fish disease diagnosticians have used this technique to identify and quantify bacterial, viral and parasitic fish pathogens such as: *Aeromonas salmonicida, Flavobacterium columnare, Renibacterium salmoninarum, Henneguya ictaluri*, Largemouth bass virus, and recently *Francisella piscicida* (now named *F. noatunensis*) in Norwegian cod (Balcazar et al. 2007; Getchell et al. 2007; Panangala et al. 2007; Suzuki & Sakai 2007; Griffin et al. 2008; Ottem et al. 2008). The high sensitivity, high specificity, and short turnaround time for results make this technique an attractive replacement method for conventional diagnostic techniques (Espy et al. 2006).

We have identified and isolated a fish pathogen, *Francisella asiatica* LADL07-285A, a clinical isolate from diseased tilapia *Oreochromis niloticu*. We then identified in this isolate homologue genes of the *F. tularensis* intracellular growth locus (iglA, iglB, iglC, and iglD). We made an insertion mutation in the iglC gene of LADL 07-285A, *Francisella asiatica*, by allelic exchange using an insertion of a selective marker, and found that the iglC mutant was attenuated using intraperitoneal and immersion challenges in tilapia. Laboratory challenge methods for inducing francisellosis in tilapia were evaluated by intraperitoneal injection and immersion with serial dilutions of *Francisella* sp. LADL 07-285A. The lethal dose 50 value, 40 days post-challenge, was $10^{-5.3}$ (~$1.2\times10^3$ CFU/fish) by intraperitoneal injection and was $10^{-4}$ ($2.3\times10^7$ CFU/ml of tank water) by immersion. The mutants retained their invasive qualities, yet were cleared by the host after a short time. We have shown that the attenuated strain provided protection against an infection of *F. asiatica* in tilapia, and believe that it would be an effective vaccine against a *Francisella asiatica* infection in other fish, for example, striped bass, hybrid striped bass, and three line grunt. In addition, the attenuated bacteria could be used to at least partially immunize fish from other species of *Francisella*. We also discovered that the attenuated vaccine may be used not only to vaccinate fish against *Francisella*, but also to serve as a vector to present antigens from other pathogens to the fish immune system, therefore serving as vaccines against other known pathogens, for example *Salmonella*, of fish as well. We have also developed a highly sensitive and specific assay that can be used for the specific identification of *F. asiatica* in fish.

Figure 1:
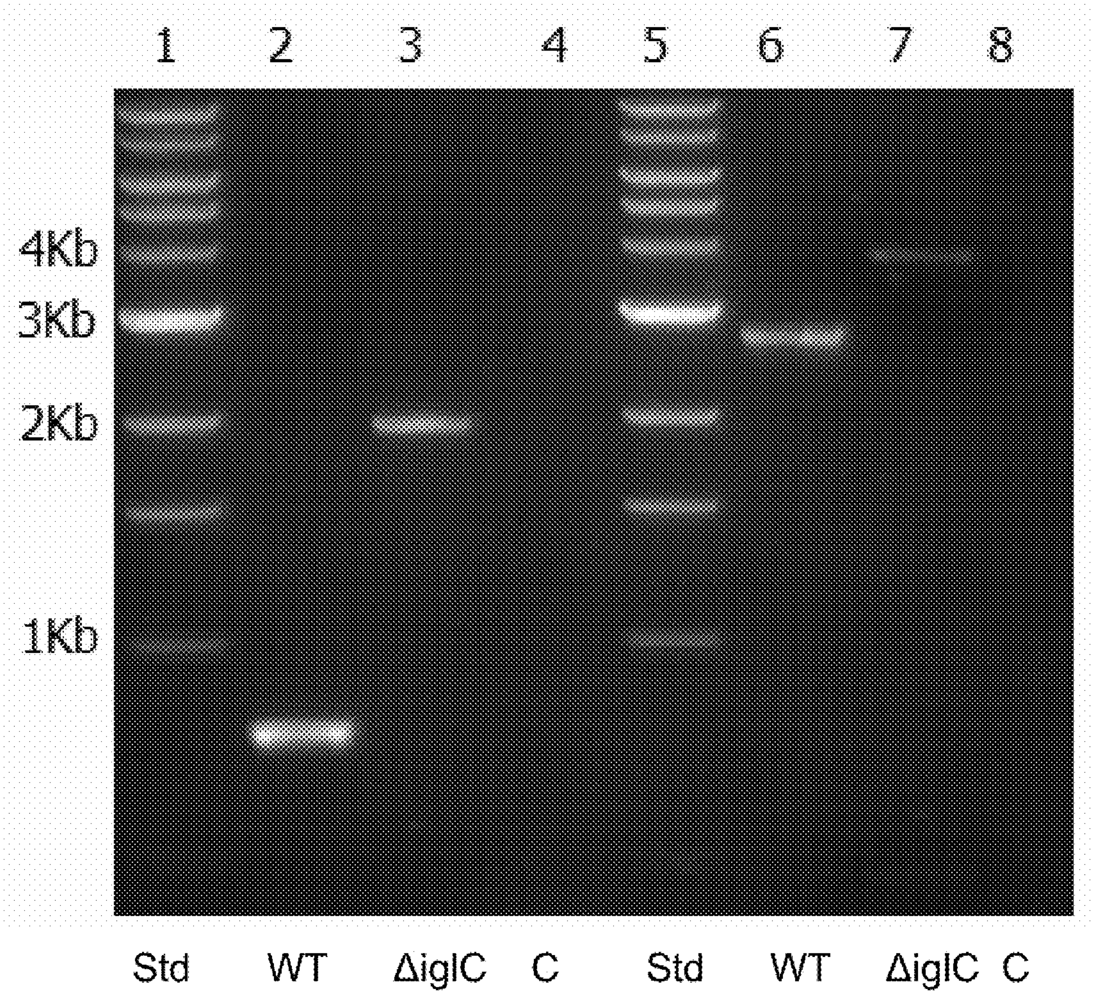
FIG. 1 illustrates the results of PCR amplification of iglC from wild type and isogenic mutant *Francisella asiatica* LADL 07-285A. Lanes 1 and 5 represent the standard 1 kb Ladder (STD). Lanes 2 and 6 represent the PCR amplification of the iglC gene from *Francisella* sp. LADL 07-285A (WT) using primer sets F46-F47 (SEQ ID NOS: 3 and 4) and F31-F38 (SEQ ID NOS: 12 and 154), respectively. Lanes 3 and 7 represent the PCR amplification of isogenic mutant strain *Francisella* sp. LADL 07-285A ΔiglC (ΔiglC) using primer sets F46-F47 and F31-F38, respectively. Lanes 4 and 8 represent the control lanes (C) using water.

We examined the presence of homologues to the Igl virulence genes in non-tularensis fish pathogenic *Francisella asiatica*, and discovered a useful method for allelic exchange using PCR products to mutate *F. asiatica*. We then created an attenuated iglC mutant which was tested using both intraperitoneal and immersion challenges in tilapia (*Oreochromis* sp.). We also examined intraperitoneal and immersion infectivity trials, to induce francisellosis in tilapia (*Oreochromis* sp.), and report the dose required to cause mortality in 50% of the fish ($LD_{50}$) of this important emergent fish pathogen. We have created an attenuated bacterial mutant which can be used as a vaccine to protect fish from infection with *F. asiatica*. The *F. asiatica* strain utilized, LADL 07-285A, was isolated from tilapia from Costa Rica, Central America, at the Louisiana Aquatic Diagnostic Laboratory, LSU School of Veterinary Medicine, and was confirmed by molecular analysis as *F. asiatica* and exhibited 99% identity with other fish pathogenic *Francisella* spp. After genetic comparison, the isolates from Costa Rica were found to belong to the same species as the earlier isolates from Japan and Taiwan, both of the species *Francisella asiatica*.

In other work, we examined the interaction of *Francisella asiatica* wild type and a *F. asiatica* ΔiglC mutant strain with fish serum and head kidney derived macrophages (HKDM) of tilapia. Both the wild type and the mutant strains were shown to be resistant to killing by normal and heat-inactivated serum. The wild type *F. asiatica* was able to invade tilapia head kidney derived macrophages and replicate vigorously within them, causing apoptosis and cytopathogenicity in the macrophages 24 and 36 h post infection. In contrast, the *F. asiatica* ΔiglC mutant was found to be defective for survival, replication, and the ability to cause cytopathogenicity in HKDM, but the ability is restored when the mutant is complemented with the iglC gene. Uptake by the HKDM was partially mediated by complement and partially by macrophage mannose receptors, as demonstrated by in vitro assays. See, E. Soto et al. 2010b; and U.S. Provisional Application 61/242,111.

EXAMPLE 1

Isolation of *Francisella* sp.

Materials and Methods

Fish history: Approximately 50 tilapia, *Oreochromis niloticus* (L.), cultured in the province of Alajuela, Costa Rica, were received and analyzed by the Pathology Service of the School of Veterinary Medicine of the Universidad Nacional de Costa Rica during August-October 2007. Fifteen euthanized fish were sent to the Louisiana Aquatic Diagnostic Laboratory (LADL) at Louisiana State University-School of Veterinary Medicine (LSU-SVM), Baton Rouge, La., for further analysis.

Histological analysis: At LSU-SVM, the gill, spleen, kidney, liver, heart, brain, ovary, testis and muscle were fixed in neutral buffered 10% formalin; processed by standard methods, and stained with haematoxylin and eosin and Giemsa stain, and examined by light microscopy. Unless otherwise stated, all chemicals and materials were commercially purchased from Sigma Chemical Co., St. Louis, Mo.

Isolation, media and growth conditions for bacteria: Fish tissues (spleen, anterior kidney and liver) were aseptically collected and used for bacteriological analysis by streaking on different agar media. Commercially available media tested for primary recovery of bacteria from fish tissue smears included: trypticase soy agar ("TSA") with 5% sheep blood, cystine heart agar ("CHA") with rabbit blood and antibiotics, chocolate agar/improved Thayer-Martin biplate (Remel, Lenexa, Kans.), chocolate II agar (GC II agar with haemoglobin and Isovitalex), and modified Thayer-Martin agar (Becton Dickenson (BD) BBL, Sparks, Md.). Two types of agar plates used as primary isolation media were prepared in the media preparation laboratory at LSU-SVM: cystine heart agar supplemented with bovine haemoglobin solution (CHAH) (Becton Dickenson (BD) BBL, Sparks, Md.) and Mueller-Hinton base supplemented with 3% foetal bovine serum, 1% glucose and 0.1% cystine. Polymixin B 100 units $mL^{-1}$ and/or ampicillin 50 μg $mL^{-1}$ were added to the media to select against secondary contaminants.

Plates were incubated at 22-25° C. for 2-5 days. Colonies observed from primary isolation agar plates were re-plated for purity of culture under the same conditions. Once single colonies were observed and purity of the isolate determined, the isolate was re-suspended in liquid medium as reported by Baker, Hollis & Thornsberry (1985) with modifications. The liquid medium consisted of a modified Mueller-Hinton II cation adjusted broth supplemented with 2% IsoVitaleX (BD BBL) and 0.1% glucose (MMH). Broth cultures were grown overnight at 22° C. in a shaker at 175 rpm, and bacteria were frozen at −80° C. in the broth media containing 20% glycerol for later use.

Three different isolates (obtained from three different fish) were tested at different culture temperatures; 15, 20, 22, 25, 28, 30, 32, 35 and 37° C. on CHAH for a period of 7 days to find the in vitro optimal growth temperature of the bacteria. The isolate labeled 07-285 A was used to make the attenuated mutant bacteria.

DNA extraction: Two isolates (07-285A and 07-285B) recovered from fish as described above were used for molecular analysis. A loop of the bacterium was suspended in 400 μL of sterile water, washed and centrifuged at 3000×g for 5 min, and re-suspended in 200 Dulbecco's phosphate-buffered saline (PBS; Gibco/Invitrogen, Carlsbad, Calif.). The bacterial suspension was subjected to DNA extraction and purification as per the manufacturer's protocol using the High Pure PCR Template Preparation Kit (Roche). DNA was stored at 4° C. until further use.

PCR and 16S rRNA gene sequence: Two different sets of primers were used during the study to amplify gene sequences important in identification of the genus *Francisella*. The 50 μL *Francisella*.-specific PCR reaction was composed of 0.2 μM of each primer (F11, 5'-TAC CAG TTG GAA ACG ACTGT-3') (SEQ ID NO:17) and F5,5'-CCT TTT TGA GTT TCGCTC C-3') (SEQ ID NO:18) developed by Forsman, Sandtstrom & Sjostedt (1994), 0.2 mM of dNTPs, 2.5 mM $MgCl_2$, 5 U of Taq DNA polymerase (Applied Biosystems-Roche, Foster City, Calif.), 1× PCRx Amp buffer (Invitrogen, Carlsbad, Calif.), 1× PCRx Enhancer solution (Invitrogen) and approximately 200 ng of template DNA. Cycling conditions consisted of an initial denaturation step of 3 min at 94° C., followed by 35 cycles of 30 s at 94° C., 60 s at 60° C., and 60 s at 72° C., with a final extension step of 5 min at 72° C. performed in a Perkin Elmer GeneAmp PCR System 2400 (PerkinElmer Life and Analytical Sciences, Inc., Waltham, Mass.).

The 50 μL universal eubacterial 16S rRNA PCR reaction was composed of 0.5 μM of each primer (F1,5'-GAG TTT GAT CCT GGC TCAG-3' (SEQ ID NO:19) and R13,5'-AGA AAG GAG GTG ATC CAG CC-3') (SEQ ID NO:20) (Dorsch & Stackebrant 1992), 0.2 mM of dNTPs, 2.5 U of Taq DNA polymerase, 1× buffer H (Invitrogen), and approximately 200 ng of template DNA. Cycling conditions consisted of an initial denaturation step of 30 s at 94° C., followed by 30 cycles of 30 s at 94° C., 60 s at 58° C., and 90 s at 72° C., with a final extension step of 7 min at 72° C. in a Perkin Elmer GeneAmp PCR System 2400. The PCR products were subjected to electrophoresis on a 1% agarose gel and stained with SYBR® Safe DNA gel stain (Invitrogen).

Amplicons for sequencing were purified with the QiaQuick PCR Cleanup Kit (Qiagen, Valencia, Calif.) as directed by the manufacturer and were sequenced on an Applied Biosystems 3130 Genetic Analyzer using PCR primers (F11-F5) and (F1-R13).

Experimental challenges: In order to fulfill Koch's postulates, experimental infections were performed by intraperitoneal injection (IP) and gill spraying (GS) with the *Francisella asiatica* Costa Rica isolate LADL07-285A. This isolate, recovered from cultured infected tilapia in Costa Rica was grown in CHAH at 25° C. for 72 h. Cells were harvested, suspended in 5 mL of MMH broth, and incubated in a shaking incubator overnight at 22° C. to obtain a final optical density at 600 nm ($OD_{600}$) of 0.48. Enumeration of the bacteria was done by the drop plate method with 50 μL drops of each 10-fold dilution placed on cystine heart agar with haemoglobin. Resulting colony forming units per mL (CFU $mL^{-1}$) were determined.

Experimental infection of naïve *O. niloticus* (average length ~9.0 cm and average weight ~18.9 g) was tested by the IP and GS exposure routes. The fish were obtained from a source considered to be free of *Francisella* infection (TilTech Aquafarm, Robert, La.) and were found to be negative for francisellosis by culture of spleen and head-kidney smears and by PCR, prior to use in the study. Fish were maintained in 3 different tanks (10 fish per tank), representing the 2 different challenge methods and a control tank at 23-25° C. Prior to challenge, all fish were anaesthetized with MS-222 (100 mg $L^{-1}$). The IP challenge fish received a 0.1 mL injection of the bacterial suspension (~$10^7$ CFU/fish). The GS challenge fish were sprayed with 0.1-0.2 mL of the bacterial suspension, and left out of the water for approximately 15 s. Control fish were treated in a similar manner, but received 0.1 mL of sterile MMH broth.

Following each challenge exposure, the fish were placed in the respective tanks and mortality was recorded every 12 h for 10 days. Dead and moribund fish were subjected to a complete clinical, bacteriological and histopathological examination. The identity of isolated bacteria was confirmed by PCR.

EXAMPLE 2

Isolation of *Francisella asiatica* from Fish and Challenge Testing

Cystine heart agar supplemented with bovine haemoglobin solution and antibiotics, the modified Thayer-Martin agar, and CHA with rabbit blood and antibiotics were useful for the primary isolation of *Francisella asiatica* from the spleen and kidneys of diseased fish. The chocolate agar/improved Thayer-Martin biplate, chocolate II agar, and the Mueller Hinton base supplemented with 3% foetal bovine serum, 1% glucose and 0.1% cystine were not suitable for primary isolation, although sub-culture could be successfully performed on these agars. The *F. asiatica* failed to grow on TSA agar with 5% sheep blood. The strains of *F. asiatica* isolated from tilapia from Costa Rica by the LADL were designated as strains LADL07-285A and LADL07-285B.

Growth of *Francisella asiatica* was visible on CHAH, 36-48 h post-inoculation and colonies were grey, smooth and convex. Optimal growth of *F. asiatica* occurred at 28-30° C., but growth was present from 20-28° C. after four days of incubation. Growth at 22-25° C. was slower than at 28° C., and no growth was observed at 15° C. or at 33° C. By light microscopy, the morphology of the bacterium was extremely pleomorphic, non-motile and very small in size (~0.5-1 μM wide).

The isolates recovered from the infected spleen and kidneys yielded the appropriately amplified PCR products of 1150 bp using the *Francisella* genus-specific primers F11 (SEQ ID NO:17) and F5 (SEQ ID NO:18) (Data not shown). When using the universal eubacterial 16S rRNA primers F1 (SEQ ID NO:19) and R13 (SEQ ID NO:20), a 1384 bp product was amplified from LADL07-285A and LADL07-285B. The sequence for isolate *F. asiatica* LADL07-285A was deposited in GenBank under the accession number EU672884.

Intraperitoneal injection of *F. asiatica* LADL07-285A of ~$10^7$ CFU/fish caused 100% mortality in naïve tilapia by 72 h post-inoculation. Tilapia exposed to bacteria by gill immersion also exhibited high mortality (80%), but this occurred gradually over the duration of the study (10 days). The clinical signs presented in the experimentally challenged fish were consistent with those found in the naturally infected cases. In the IP injection group, a more acute onset of the disease was seen and most fish died in a short period of time (<48 h post-challenge). The clinical signs in the acutely infected fish were bloody ascites, slight swelling of the spleen and kidney, with increased number and size of melanomacrophage centres but no granulomas were seen. Numerous small coccobacilli were present both intracellularly and extracellularly in the tissues. Fish exposed by gill immersion presented with a more subacute to chronic form of the disease, showing signs of anorexia and erratic swimming behavior. At necropsy, splenomegaly and renomegaly were pronounced and granulomas were numerous in both organs. Numerous intra and extracellular bacteria were observed microscopically in gills, spleen, and anterior and posterior kidney. *F. asiatica* was re-isolated from both challenged groups by inoculating homogenates of spleen and posterior kidney on CHA supplemented with bovine haemoglobin solution and antibiotics. The isolates were confirmed by PCR as members of the genus *Francisella.*

At the completion of the experimental challenge, all control fish were alive and no bacterial infection was detected by bacteriological, histopathological or molecular analysis.

EXAMPLE 3

Materials and Methods for Development of Attenuated Bacterial Vaccine

Bacterial strains and growth conditions: Strains, plasmids and primers used are listed in Table 1. *Francisella asiatica* LADL 07-285A was isolated from cultured tilapia (*Oreochromis* sp.) as described above. *F. asiatica* LADL 07-285A was grown in Cystine Heart Agar supplemented with bovine hemoglobin solution (BD BBL, Sparks, Md., USA) (CHAH) for 48 h at 28° C. A liquid culture medium consisted of a modified Mueller-Hinton II cation adjusted broth supplemented with 2% IsoVitaleX (BD BBL, Sparks, Md., USA) and 0.1% glucose (MMH). Broth cultures were grown overnight at 25° C. in a shaker at 175 rpm, and bacteria were frozen at −80° C. in the broth media containing 20% glycerol for later use. Polymixin B (100 units/ml) and ampicillin (50 μg/ml) were added when needed to make the primary isolation media selective to aid in recovery of the bacteria from fish tissues; and kanamycin (15 μg/ml) was used for recovery of transformed bacteria following electroporation. *Escherichia coli* XL1 Blue MRF' was grown using Luria-Bertani broth or agar for 16-24 h at 37° C. and supplemented with kanamycin (50 μg/ml) when needed to recover the plasmid containing bacteria after electroporation.

TABLE 1

Description of strains, plasmids and primers

| | Characteristics | Source (if any) |
|---|---|---|
| Bacterial Strain | | |
| *Francisella asiatica* 07-285A | Isolated from tilapia | |
| *E.coli* XL1 Blue MRF | | |
| Plasmids | | |
| pEN1 | $Km^R$ | Ludu et al., 2008-a |
| pBS | High copy number plasmid | Stratagene |
| pBSiglC | High copy number plasmid-wild type iglC | |
| pBSΔiglC | High copy number plasmid with ΔiglC , $Km^R$ | |
| Primers used for mutagenesis | | |
| F-40 (iglC-XhoI) | 5' aatt*ctcgag*tgttggtgctgagcaaattc 3' (SEQ ID NO: 1) | |
| F-41 (iglC-SpeI) | 5' aattta*actagt*cagcacagcatacaggcaag 3' (SEQ ID NO: 2) | |
| F-46 (iglC) | 5' tgttggtgctgagcaaattc 3' (SEQ ID NO: 3) | |
| F-47 (iglC) | 5' cagcacagcatacaggcaag 3' (SEQ ID NO: 4) | |
| F-12 FA1451-1 | 5' ttttgggttgtcactcatcgt 3' (SEQ ID NO: 5) | Liu et al., 2007 |
| F-13 FA1451-2 | 5' cgctataaccctcttcattt 3' (SEQ ID NO: 6) | |
| Primers used for amplification of iglABCD homologues | | |
| F36iglA | 5' gggaagatcggtagatgcaa 3' (SEQ ID NO: 7) | |
| F37iglA | 5' cgagtagtgctctgatttctgg 3' (SEQ ID NO: 8) | |
| FA22iglB | 5' gtcagaagagtaaataatggtgt 3' (SEQ ID NO: 9) | Liu et al., 2007 |
| FA23iglB | 5' ggctctatactaatactaaaagc 3' (SEQ ID NO: 10) | Liu et al., 2007 |
| F30iglBinternal | 5' tttagttattattcgcaccg 3' (SEQ ID NO: 11) | |
| F31iglBinternal | 5' caggaagtttgtcaagatga 3' (SEQ ID NO: 12) | |
| FA26iglC | 5' gagtttgaaggaatgaatactacaatga 3' (SEQ ID NO: 13) | |
| FA27iglC | 5' gagccatcttcccaataaatcctt 3' (SEQ ID NO: 14) | |
| F38iglD | 5' gctggagctattgcctttctt 3' (SEQ ID NO: 15) | |
| F39iglD | 5' tgctatcctctatctttgcaggt 3' (SEQ ID NO: 16) | |

Identification of *F. tularensis* operon iglABCD homologue in *Francisella asiatica* LADL 07-285A: The complete genome sequences of *F. philomiragia* subsp. *philomiragia* ATCC 25017 (GeneBank accession number CP000937), *F. tularensis* subsp. *novicida* U112 (GeneBank accession number CP000439), and partial genome sequences of *F. piscicida* strain GM2212 (GeneBank accession number EU492905), available from the National Center for Biotechnology Information (NCBI), were used to compare the iglABCD regions. Previously published *F. tularensis* primers to these genes were also compared and were used as a template to design primers to amplify homologous regions from the *F. asiatica* LADL 07-285A chromosomal DNA by polymerase chain reaction (PCR). PCR amplicons for sequencing were purified with the QiaQuick Minelute PCR Cleanup Kit (Qiagen, Valencia, Calif., USA) as directed by the manufacturer, and were sequenced on an Applied Biosystems 3130 Genetic Analyzer using the PCR primers in Table 1.

The sequences from the *F. asiatica* LADL 07-285A iglABCD genes and the corresponding amino acid sequences were compared with those stored in the NCBI database using the BLASTN and BLASTP program, with default settings.

Electroporation: Electrocompetent *E. coli* and *F. asiatica* LADL 07-285A were prepared following Maier et al. (2004) with some modifications. Briefly, *E. coli* was aerobically grown until mid-logarithmic stage ($OD_{600}$ 0.7), and the cells were prepared by washing 2 times in water followed by 1 wash in 10% glycerol. The electrocompetent *E. coli* were electroporated using a BioRad Gene Pulser Controller, in a 2 mm electroporation cuvette (BTX Harvard apparatus, Holliston, Mass.). The pulser was set at a voltage of 2.5 kV, a capacitance of 25 uF, and a resistance of 200Ω Immediately after electroporation, cells were suspended in 1 ml of LB-broth; and incubated with shaking for 1 h at 37° C. After the 1 h incubation period, *E. coli* was plated on LB agar with kanamycin (50 ug/ml).

*Francisella asiatica* LADL 07-285A was grown aerobically until late-logarithmic stage ($OD_{600}$ 0.6), and the cells were prepared by using 0.5 M sucrose. The electrocompetent *F. asiatica* were electroporated using the Gene Pulser in a 2 mm cuvette. The pulser was set at a voltage of 2.5 kV, a capacitance of 25 uF, and a resistance of 600Ω. Immediately after electroporation, cells were suspended in 1 ml of MMH-broth, and incubated with shaking for 4 h at 28° C. After the 4 h incubation period, *F. asiatica* was plated on CHAH with Kanamycin (15 ug/ml).

Mutant and plasmid construction: A fragment of approximately 850 base pairs corresponding to a portion of the iglB and iglC genes from *F. asiatica* LADL-07-285A was PCR amplified using primers F-40 (SEQ ID NO: 1) and F-41 (SEQ ID NO: 2) (Table 1), which contain XhoI and SpeI sites, respectively. All enzymes used during the study were supplied by New England Biolabs, Inc. (Ipswich, Mass.), and were used under the conditions recommended by the manufacturer. The PCR product was cleaved with these two endonucleases and ligated into the high copy number plasmid pBluescript SK (pBS), resulting in plasmid pBS-iglC. The plasmid was electroporated into *E. coli*, amplified, and then purified from the bacterium using the QIAprep Spin Miniprep Kit (Qiagen, Valencia, Calif., USA) following the manufacturers protocol.

Plasmid pEN1, constructed and donated by Ludu et al. (2008-a), contains a Tn903 Kanamycin cassette linked to *Francisella novicida* promoter derived from the region upstream of gene FTN_1451 (Km-P) (Gallagher et al. 2007). Purified pEN1 plasmid was digested with PstI to release the Km-P cassette. Other known selection markers could be used instead of Kanamycin, for example, other antibiotics, color-expressing markers (e.g., green fluorescent protein (GFP) or M-cherry), and heat selection markers.

For the construction of pBS-ΔiglC, plasmid pBS-iglC was digested with PstI endonuclease, which cuts once in the iglC gene. The 1100 bp KmP cassette was ligated into the unique PstI site in pBS-iglC, resulting in pBS-ΔiglC. The resulting insertion was verified by sequencing.

EXAMPLE 4

Identification of IglABCD Operon

The deduced amino acid products of the *Francisella asiatica* LADL 07-285A iglA gene have 95, 92 and 88% similarities to the intracellular growth locus protein A of *F. philomiragia* subsp. *philomiragia, F. piscicida*, and *F. tularensis* subspecies respectively. The amino acid sequences of the *F. asiatica* LADL 07-285A proteins IglB, IglC and IglD showed identity of 97, 95 and 92% (IglB), 93, 90 and 89% (IglC) and 94, 92 and 80% (IglD) respectively to the intracellular growth locus proteins found in *F. philomiragia, F. piscicida*, and *F. tularensis* species, respectively. The G+C content found in the iglABCD operon from *F. asiatica* LADL 07-285A (GeneBank accession number FJ386388) was 31%. Overall DNA comparison between *F. asiatica* LADL 07-285A, *F. philomiragia* subsp. *philomiragia* and *F. tularensis* subsp. *novicida* U112 iglABCD operon, showed that the *F. asiatica* fish pathogen shares 94% identity to *F. philomiragia* and 83% identity with *F. tularensis* subsp. *novicida*. The iglABCD operon of the three members of the genus *Francisella* were in the same orientation and arrangement.

EXAMPLE 5

Generation of a *Francisella asiatica* LADL 07-285A iglC Mutant

An insertion mutation made in the iglC gene of *F. asiatica* LADL 07-285A by allelic exchange using Km-P was found to have approximately 400 base pairs of flanking sequences on either side of the insertion site. Insertion of Km-P was confirmed by PCR using 2 different set of primers and DNA sequencing. Primer sets F46-F47 (SEQ ID NOS.: 3 and 4) and F31-F38 (SEQ ID NOS: 12 and 15) were used to verify the insertion and position of the 1100 bp Km-P cassette in iglC (FIG. 1). Primers used for amplification of the FA-1451 promoter region were also used to sequence the inside region of the insertion, and verify the presences of the promoter in the mutant. FIG. 1 illustrates the results of PCR amplification of iglC from wild type and isogenic mutant *F. asiatica* LADL 07-285A. Lanes 1 and 5 represent the standard 1 kb Ladder. Lanes 2 and 6 represent the PCR amplification of the iglC gene from *F. asiatica* sp. LADL 07-285A using primer sets F46-F47 (SEQ ID NOS: 3 and 4) and F31-F38 (SEQ ID NOS: 12 and 15), respectively. Lanes 3 and 7 represent the PCR amplification of isogenic mutant strain *F. asiatica* LADL 07-285A ΔiglC using primer sets F46-F47 (SEQ ID NOS: 3 and 4) and F31-F38 (SEQ ID NOS: 12 and 15), respectively. Lanes 4 and 8 represent the control lanes using water.

The resulting *F. asiatica* LADL 7-285A ΔiglC strain had no obvious morphological differences from the wild type strain and growth characteristics were identical to those of the parental strain in broth and on agar media. The insertional mutagenesis protocol followed, allowed the selection for a double recombination in the *F. asiatica* LADL 07-285A iglC gene. Kanamycin was used as the selective antibiotic resistance marker due to the natural kanamycin susceptibility of the *Francisella* sp. strain used in this study (data not shown). Other known selection markers could be used instead of Kanamycin, for example, other antibiotics, color-expressing markers (e.g., green fluorescent protein (GFP) or M-cherry), and heat selection markers.

A sample of the novel *Francisella* sp. LADL 07-285A ?iglC strain, designated *Francisella asiatica* ? igl C (LSU F1) was deposited with the American Type Culture Collection (ATCC), 10801 University Boulevard, Manassas, Va. 20110-2209, United States on Aug. 26, 2010, and was assigned ATCC Accession No. PTA-11268. This deposit was made under the Budapest Treaty.

EXAMPLE 6

Tilapia LD-50 Virulence Assays

Preparation of bacterial stock culture and enumeration: *Francisella asiatica* LADL 07-285A was cultivated in MMH in a shaking incubator at 175 rpm overnight at 25° C. The bacteria were then pelleted and the concentrations were adjusted to ~$2.3\times10^9$ CFU/ml in Dulbecco's phosphate-buffered saline (PBS; Gibco/Invitrogen, Carlsbad, Calif.). Tenfold dilutions of this stock were then made in sterile saline. Actual bacterial numbers delivered by injection and by immersion were determined by colony counts on CHAH plates. Enumeration of the bacteria was done by placing 50 µl drops of each 10-fold dilution on CHAH and counting the resulting colonies after 72 h incubation at 25° C. The dilution which produced countable colonies (10-50 per drop) was then used to calculate the CFU/ml in the stock suspension.

Fish and systems: Naïve tilapia (average length ~9.0 cm and average weight ~18.9 g) were obtained from a source believed to be free of *Francisella* infection (TilTech Aquafarm, Robert, La.), and a sub-sample of the population was confirmed as negative for *Francisella* bacteria by culture on CHAH and PCR, prior to use in the study. Groups of 10 fish were placed in 90 L tanks with filtered recirculating water flow (one tank per treatment). Water temperature was maintained in the range of 23-25° C. throughout the study, and fish were fed daily with a commercial 4.7 mm pelleted fish feed (Cargill, Franklinton, La.) at 5% body weight. The fish were allowed to acclimate for at least 2 weeks prior to challenge. At challenge, all fish were anesthetized with MS-222 (100 mg/l) prior to handling.

Intraperitoneal Injection (IP): From the initial bacterial concentration in the stock suspension ($2.3\times10^9$ CFU/ml in PBS), 10 serial dilutions in PBS were prepared. Each fish per treatment was injected with 0.1 ml of the bacterial suspension. Fish in the control tank were injected with 0.1 sterile PBS. Mortality was recorded daily following IP injection and the $LD_{50}$ calculated for the wild type strain of *F. asiatica* LADL 07-285A.

Immersion challenge (IC): Immersion challenge was carried out in 8 different dilutions of the bacterial suspension. The IC fish were immersed in 10 L of static water containing $2.3\times10^8$, $2.3\times10^7$, $2.3\times10^6$, $2.3\times10^5$, $2.3\times10^4$, $2.3\times10^3$, $2.3\times10^2$, $2.3\times10^1$ CFU of the wild type strain of *F. asiatica* LADL 07-285A/ml of tank water for 3 h. After 3 h, fish were moved to a clean 90 L tank system with biofiltered recirculating water. Control fish were treated with sterile PBS in a similar manner.

Analysis of dead and surviving fish after challenge: Dead and surviving fish were subjected to a complete clinical and bacteriological examination. A histological evaluation was performed on splenic, hepatic and renal tissue of moribund, freshly dead and surviving fish. Severity of the disease in each treatment was determined by counting the number of granulomas in histological sections present per single 10× microscopic field from the spleen, head kidney and liver of each fish. The means of these counts were reported as relative severity in Table 2 using the following scale: severe=>20, moderate=7-20, and mild=<7. Molecular analysis by PCR was performed following the above protocol using bacterial cultures recovered from moribund and dead fish, as well as from DNA extracted from spleen tissue of fish surviving challenge. The $LD_{50}$ was calculated at days 20 and 40 by the method of Reed-Muench (Anderson 1984), following both the intraperitoneal and the immersion challenges.

In-vivo challenge with *F. asiatica* LADL 07-285A wild type and ΔiglC: The wild type and ΔiglC strains were tested for virulence by both IP and IC challenge. *F. asiatica* LADL07-285A wild type and ΔiglC isogenic strains were grown on CHAH plates at 25° C. for 72 h. Cells were harvested, suspended in 1 liter of MMH broth, and incubated in a shaking incubator overnight at 24° C. to obtain a final optical density at 600 nm ($OD_{600}$) of 0.75. Enumeration of bacteria in IP and IC challenges was accomplished by the same methods outlined in $LD_{50}$ study.

The fish were obtained from the same source, were in the same size range, and were fed the same way as described above for the $LD_{50}$ study. The challenge trials were done in 20 liter flow through tanks, however, with chlorination traps in the drain system for biosafety. Fish were maintained at 10 fish per tank, and four tanks were used per treatment with one tank serving as a non-infected control. Prior to challenge all fish were anesthetized with MS-222 (100 mg/l). Intra-peritoneal challenged fish received a 0.1 ml injection of bacterial suspension (~$3\times10^8$ CFU/fish, or ~$1.5\times10^8$ CFU/fish). The IC fish were immersed in 8 L of static water containing approximately $3.7\times10^7$ CFU/ml in tank water or $1.8\times10^7$ CFU/ml of tank water for 3 h, and then the volume of the tanks was adjusted to a maximum of 20 liters with clean dechlorinated and aerated municipal water. Control fish were treated in a similar fashion but received sterile PBS in place of the bacterial suspension.

Following each challenge exposure, mortality was recorded every 12 h for 30 d. Dead fish and survivors from each challenge were subjected to a complete clinical and bacteriological evaluation. Polymerase chain reaction was performed on DNA from bacterial cultures recovered from moribund and dead fish to confirm the presence of wild type or ΔiglC.

Statistical analysis: Data (both original and inverse sine transformed) obtained from IC and IP challenges with the *F. asiatica* LADL 07-285A wild type and ΔiglC strains were compared in an analysis of variance of a factorial arrangement of treatments with the SAS® statistical program (version 9.1.3). Where significance was found, post hoc pairwise comparisons were conducted with t tests of least squares means. Differences were considered significant at $P\leqq0.05$.

Figure 2:
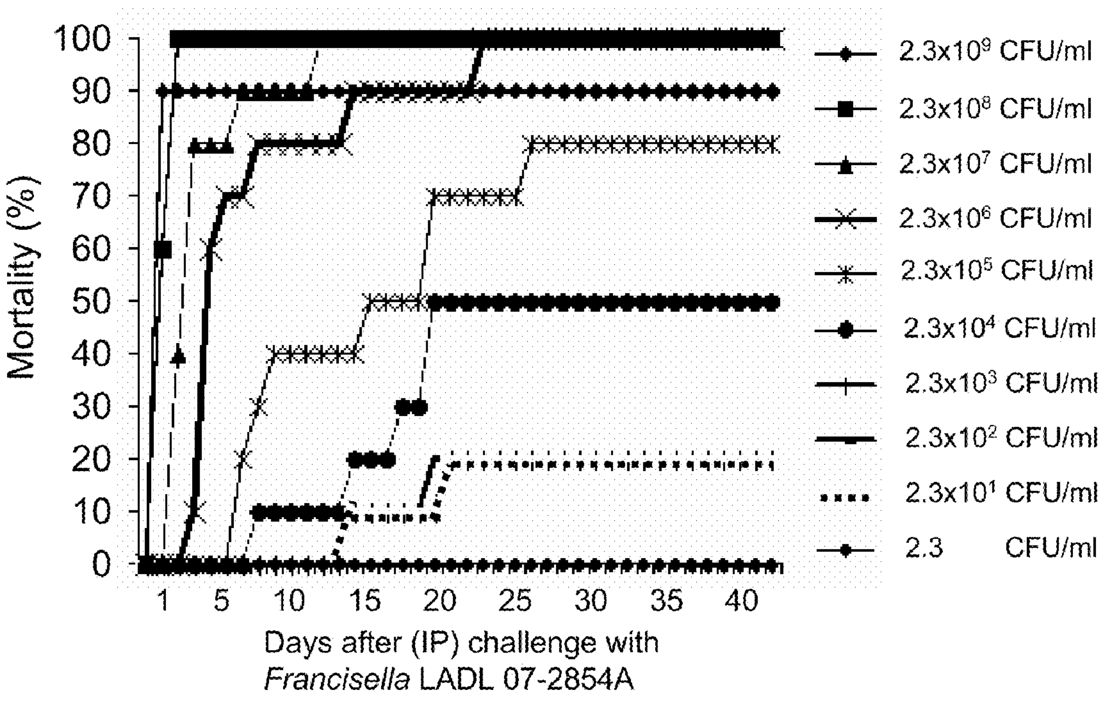
FIG. 2 illustrates the mortality rate over time of tilapia challenged with *Francisella* asiatica LADL 07-285A by intraperitoneal (IP) injection using various concentrations of the pathogen (10 fish were infected per treatment).
Figure 3:
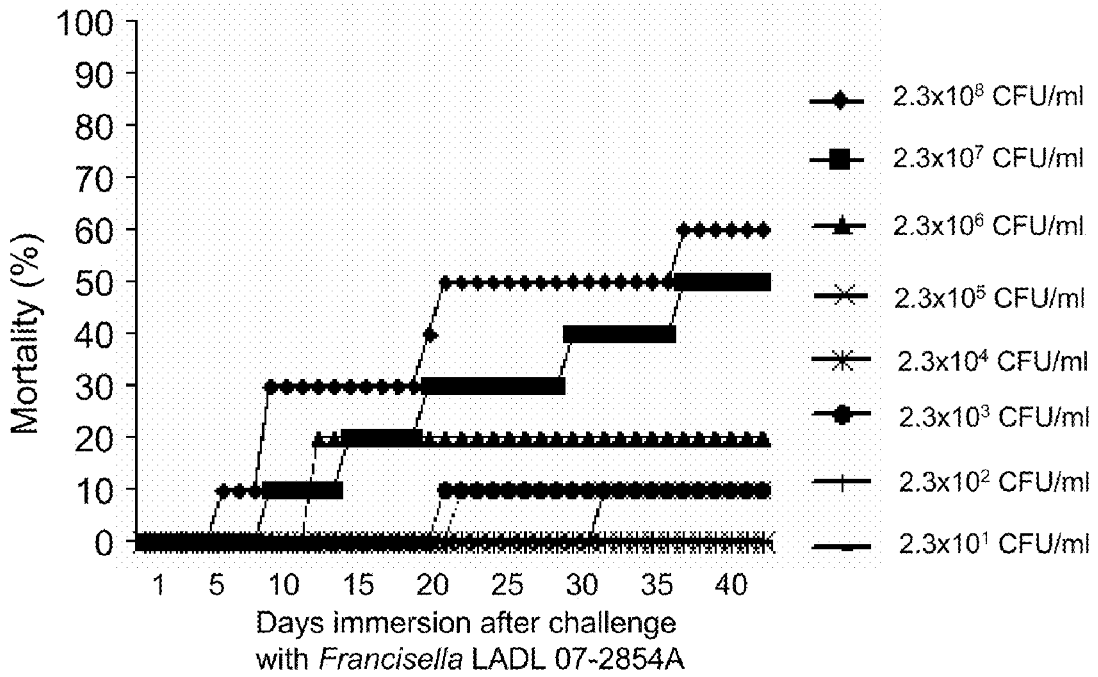
FIG. 3 illustrates the mortality rate over time of tilapia challenged with *Francisella asiatica* LADL 07-285A by immersion challenge using various concentrations of the pathogen (10 fish were infected per treatment).

Mortalities of tilapia challenged by IP or IC are shown in FIGS. 2 and 3, respectively. Based on the cumulative mortalities found at day 20 and at day 40, the observed median lethal dose ($LD_{50}$) for the IP challenged tilapia infected with *F. asiatica* LADL 07-285A was $10^{-5.1}$ (~$1.8\times10^4$ CFU/fish), and $10^{-53}$ (~$1.2\times10^4$ CFU/fish) respectively. On the other hand, the observed median lethal dose ($LD_{50}$) for the IC tilapia at day 20 and at day 40, were $10^{0.52}$ (~$6.9\times10^7$ CFU/ml), and $10^{-1}$ (~$2.3\times10^7$ CFU/ml) respectively. The least amount of bacteria required to cause mortality in the IP challenged tilapia was 23 CFU, whereas for the IC, 2.3×$10^2$ CFU/ml of tank water was necessary to cause mortality (Table 2).

TABLE 2

Summary of mortalities, bacterial isolation and severity of lesions observed 40 days post challenge with *Francisella asiatica* LADL 07-285A in $LD_{50}$ Virulence Assays.

| Challenge dose | % Mortality | Bacterial isolation from dead fish | Bacterial isolation from survivors | Survivors Spleen PCR | Mean value of granulomas in 10X microscopic field: Spleen | Head kidney | Liver |
|---|---|---|---|---|---|---|---|
| Intraperitoneal Challenge (CFU/ml of PBS) | | | | | | | |
| 2.3 × $10^9$ CFU/ml | 98.3 | Pos[a] | Pos | Pos | Moderate[d] | Mild[f] | Mild |
| 2.3 × $10^8$ CFU/ml | 98 | Pos | N/A[c] | Pos | N/A | N/A | N/A |
| 2.3 × $10^7$ CFU/ml | 97.5 | Pos | N/A | Pos | N/A | N/A | N/A |
| 2.3 × $10^6$ CFU/ml | 96.6 | Pos | N/A | Pos | N/A | N/A | N/A |
| 2.3 × $10^5$ CFU/ml | 86.3 | Pos | Pos | Pos | Severe[d] | Severe | Mild |
| 2.3 × $10^4$ CFU/ml | 57.8 | Pos | Pos | Pos | Mild | Mild | Mild |
| 2.3 × $10^3$ CFU/ml | 27.7 | Pos | Pos | Pos | Severe | Severe | Mild |
| 2.3 × $10^2$ CFU/ml | 14.2 | Pos | Pos | Pos | Severe | Moderate | Mild |
| 2.3 × $10^1$ CFU/ml | 5.8 | Pos | Pos | Pos | Severe | Moderate | Mild |
| 2.3 × $10^0$ CFU/ml | 0 | N/A | Neg[b] | Pos | Moderate | Mild | Neg |
| 2.3 × $10^{-1}$ CFU/ml | 0 | N/A | Neg | Pos | Mild | Mild | Neg |
| 2.3 × $10^{-2}$ CFU/ml | 0 | N/A | Neg | Neg | Mild | Neg | Neg |
| Control | 0 | N/A | Neg | Neg | Neg | Neg | Neg |
| Immersion Challenge (CFU/ml of tank water) | | | | | | | |
| 2.3 × $10^8$ CFU/ml | 78.9 | Pos | Neg | Pos | Severe | Severe | Mild |
| 2.3 × $10^7$ CFU/ml | 50 | Pos | Neg | Pos | Severe | Severe | Mild |
| 2.3 × $10^6$ CFU/ml | 19 | Pos | Neg | Pos | Severe | Severe | Mild |
| 2.3 × $10^5$ CFU/ml | 6.8 | Pos | Neg | Pos | Severe | Moderate | Mild |
| 2.3 × $10^4$ CFU/ml | 5.1 | Neg | Neg | Pos | Moderate | Moderate | Mild |
| 2.3 × $10^3$ CFU/ml | 4.1 | N/A | Neg | Pos | Moderate | Moderate | Mild |
| 2.3 × $10^2$ CFU/ml | 1.7 | N/A | Neg | Neg | Mild | Mild | Neg |
| 2.3 × $10^1$ CFU/ml | 0 | N/A | Neg | Neg | Mild | Mild | Neg |
| Control | 0 | N/A | Neg | Neg | Neg | Neg | Neg |

Legends:
[a]Pos = Positive
[b]Neg = Negative
[c]N/A = Not Applicable
[d]Severe = X > 20
[e]Moderate = 7 < X < 20
[f]Mild = X < 7
Surviving fish from both challenges were subjected to complete clinical, bacteriological, and histopathological examination at 40 days post challenge. Selected tissues were placed in fixative at termination of the trial.

No obvious external clinical signs were observed in the fish. Internally, the most significant gross pathological change observed was the presence of widespread, multifocal white nodules dispersed in the anterior kidney, posterior kidney, and spleen, with a marked splenomegaly and renomegaly. Histopathologically, granulomatous inflammation was present in the spleen and kidneys with large numbers of macrophages containing small pleomorphic coccobacilli.

*F. asiatica* LADL 07-285A was isolated from the spleen and kidney of dead and moribund fish from both treatments. Bacteriology, histopathological and molecular analysis (PCR) performed on the internal organs of fish from both IP and IC challenge trials are shown in Table 2.

EXAMPLE 7

Figure 4:
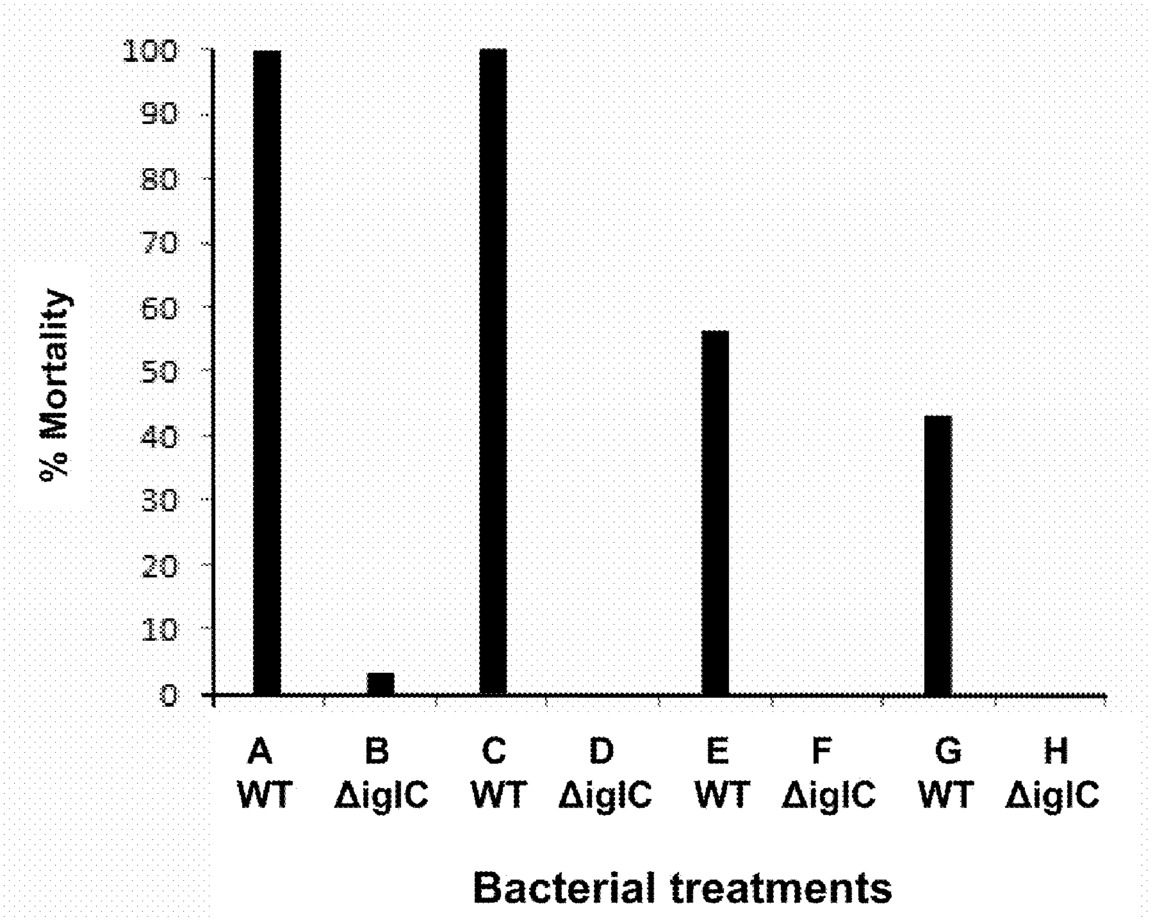
FIG. 4 illustrates the percent mortality after 30 days post challenge of tilapia (*Oreochromis* sp.) challenged by immersion challenge (IC) and intraperitoneal challenge (IP) with either *Francisella asiatica* LADL 07-285 A wild type or with *F. asiatica* LADL 07-285 A ΔiglC: Lane A, IP challenge of Wild type (~$3\times10^8$ CFU/fish); Lane B, IP challenge of ΔiglC (~$3\times10^8$ CFU/fish); Lane C, IP challenge of Wild type (~$1.5\times10^8$ CFU/fish); Lane D, IP challenge of ΔiglC (~$1.5\times10^8$ CFU/fish); Lane E, IC challenge of Wild type (~$3.7\times10^7$ CFU/ml); Lane F, IC challenge of ΔiglC (~$3.7\times10^7$ CFU/ml); Lane G, IC challenge of Wild type (~$1.8\times10^7$ CFU/ml); and Lane H, IC challenge of ΔiglC. Wild type (~$1.8\times10^7$ CFU/ml).

In-Vivo Challenge of *Francisella asiatica* LADL 07-285A Wild Type and ΔiglC To examine the role of the iglC gene on virulence in a fish model of infection, the survival rates were measured of tilapia infected with *F. asiatica* LADL 07-285A wild type (WT) and ΔiglC by two different routes of inoculation (IP and IC). After 48 h following IP injection of 0.1 ml of bacterial suspension (~3×$10^8$ CFU/fish, or ~1.5×$10^8$ CFU/fish), all the tilapia with the WT had died, while only one fish infected with the ΔiglC died 30 days post challenge. This one dead fish recovered from the challenge with the ΔiglC IP injection was not examined since it was in an advanced stage of decomposition. The difference in dosages did not show significance, while the percent mortality between wild type and mutant injected fish was significantly different ($P<0.0001$) (FIG. 4).

The fish immersed with ~3.7×$10^7$ CFU/ml of wild type bacteria in tank water had a survival percentage of 43.3%, and survival was 56.6% with the groups immersed with 1.8×$10^7$ CFU/ml. The dosages did not result in significantly different mortality ($P\leqq 0.05$). On the other hand, the fish challenged with the mutant strain had a 100% survival rate when challenged with ~3.7×$10^7$ CFU/ml and 1.8×$10^7$ CFU/ml of tank water. Percent mortality was significantly different between groups challenged with the wild type and mutant strains ($P<0.0001$) (FIG. 4).

The histopathological analysis of the fish challenged with the wild type showed the same lesions as previously described in the $LD_{50}$ challenge, with increased melanomacrophage centers, widespread granulomas and granulomatous inflammation in the spleen and head kidney. Upon gross and histopathological analysis, the fish challenged with the ΔiglC mutant by immersion challenge did not show any granulomatous lesions or increased number of melanomacrophages in the analyzed tissues. The fish challenged with the ΔiglC mutant strain by IP injection presented higher numbers of melanomacrophages in the head kidney and the spleen than the control group of fish injected with PBS at 30 days post challenge but no granulomas. The control fish immersed with PBS did not display any lesions in the tissues and organs.

The iglC mutation significantly attenuated the pathogen upon in vivo challenges, and increased the survival rates of the mutant infected fish when compared with the wild type infected fish after both IP and IC challenges. Two different administration routes (IP and IC) for challenging tilapia with *F. asiatica* were compared and the $LD_{50}$ at 20 and 40 days post-challenge reported. The IP challenge was chosen since it was an easy and quick method to accurately administer suspended bacteria, but several problems developed when administering the bacteria by this method, including the lack of exposure of the bacteria to innate immune protection present in the skin, gills and other mucosa. As was expected, an acute onset of the disease was observed, with high mortalities and few clinical signs in the fish receiving the higher dosage. It was surprising that a low dose of bacteria, ~0.23 CFU injected into the peritoneum of the fingerlings, was able to cause mortalities. Even more surprising was the amount and severity of lesions (granulomas), caused by a very low number of bacteria (~1 CFU/fish), in important hematopoietic and osmoregulatory organs like the spleen and the anterior kidney. Survivors of this treatment were observed with significant lesions in spleen, head kidney and liver, which not only impair the fish's ability to osmoregulate, but also immunosuppress them by direct damage of their hematopoietic organs making them more susceptible to other important and common tilapia diseases seen in culture facilities such as streptococcosis and columnaris disease.

Figure 5A:
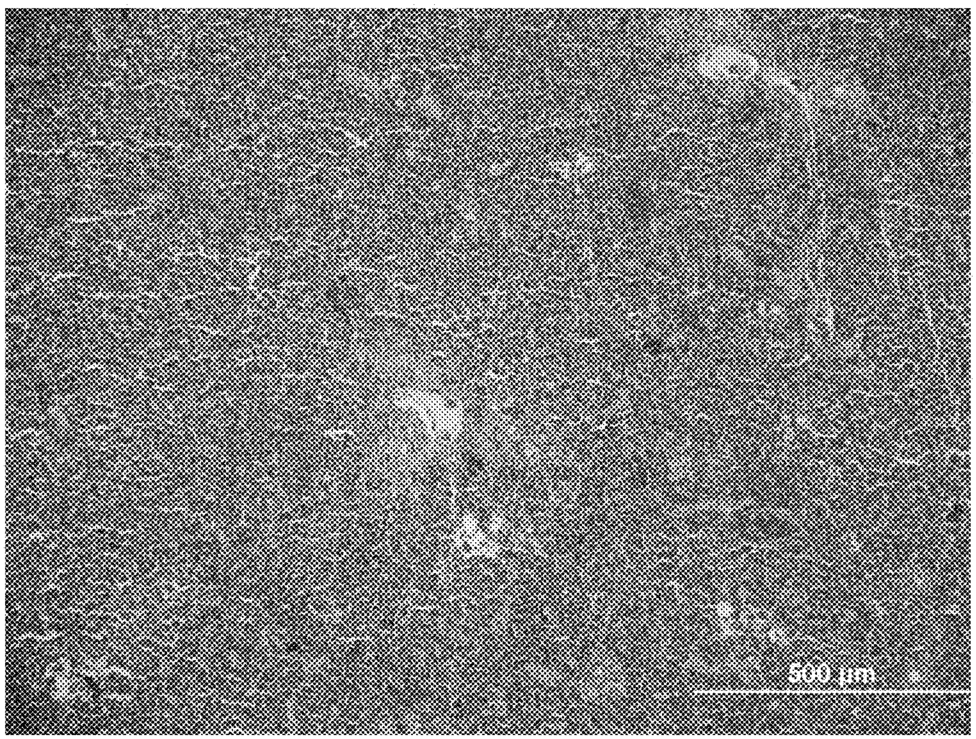
FIG. 5A is a histological photomicrograph of un-infected tilapia spleen 40 days post infection stained with H&E, showing a normal splenic parenchyma and stroma.
Figure 5B:
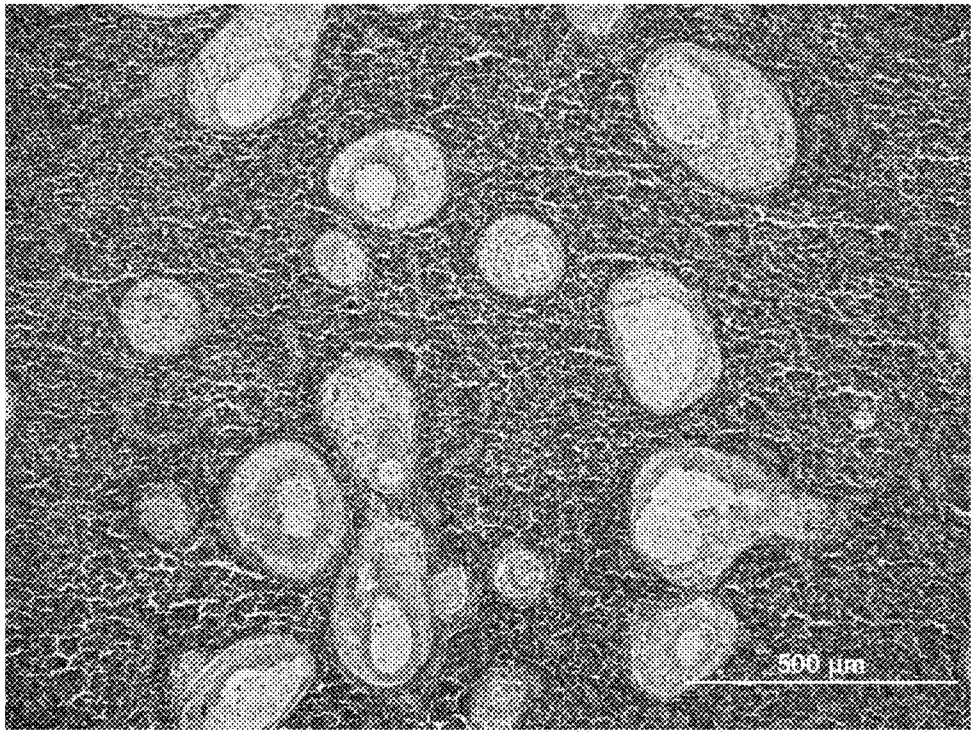
FIG. 5B is a histological photomicrograph of a severely infected tilapia spleen 40 days post infection with *Francisella asiatica* stained with H&E, showing widespread multifocal granulomatous lesions with mixed inflammatory infiltrates (23 CFU/ml immersion exposure).

The IC challenge route was chosen because it more closely resembles a natural infection. The fact that the bacteria have to come into close contact with the innate immune system present in skin, gills, gastrointestinal mucosa, etc., more closely resembles the way the disease progresses in nature. As expected, the amount of bacteria needed to cause mortality was higher than in the IP treatment, and the onset of the disease was more sub-acute to chronic, presenting anorexia, change in coloration, and pale gills. A dose of $2.3\times10^2$ CFU/ml of tank water was needed to cause mortality in the immersed fish, but when analyzing histopathological lesions of the survivors, it was evident that even a dose of 23 CFU/ml of tank water was able to cause significant lesions in the spleen and head kidney (FIG. 5). The experiment was terminated 40 days after exposure to the bacterium, but we suspect that the survivors of this trial may become carriers of the pathogen as in seen in natural infections.

Thus, the first identification of homologous genes of the *F. tularensis* pathogenicity island in the fish pathogenic *Francisella* spp. has been reported, and an easy and reliable method for mutagenesis of this fastidious pathogen has been developed. Data from challenge trials indicate that mutation of iglC results in a less virulent pathogen. Based on the homology of the iglC gene in *Francisella*, we believe that other fish pathogenic *Francisella* could be attenuated by a similar process to produce a ΔiglC mutant as discussed above.

EXAMPLE 8

Attenuated *F. asiatica* iglC Mutant Induced Protective Immunity

Part 1—Materials and Methods

Bacteria: *Francisella asiatica* LADL 07-285A WT was isolated from cultured tilapia (*Oreochromis* sp.) as described above. The ΔiglC mutant isolate was made by homologous recombination using a PCR product, and its attenuation was demonstrated in vivo and in vitro as shown above. *F. asiatica* isolates were grown in cysteine heart agar supplemented with bovine hemoglobin solution (CHAH) (Becton Dickenson (BD) BBL, Sparks, Md., USA) for 48-72 h at 28° C. The liquid medium consisted of Mueller-Hinton II cation adjusted broth supplemented with 2% IsoVitaleX (BD BBL, Sparks, Md., USA) and 0.1% glucose (MMH) as described in Baker et al. 1985. Broth cultures were grown overnight at 25° C. in a shaker at 175 rpm, and bacteria were frozen at −80° C. in the broth media containing 20% glycerol for later use. *Escherichia coli* DH5a was grown using Luria-Bertani broth or agar for 16-24 h at 37° C.

Preparation of sonicated *F. asiatica* lysate for ELISA. Approximately $1\times10^{12}$ CFU of *F. asiatica* were harvested from 500 ml of broth culture by centrifugation at 1,500×g for 10 min at 4° C. in a GSA rotor in an accuspin 3R refrigerated Centrifuge (Fisher Scientific). The pellet was washed three times with Dulbecco's phosphate-buffered saline (PBS; Gibco/Invitrogen, Carlsbad, Calif.), followed by centrifugation at 1,500×g for 10 min. Following the final wash, the pellet was resuspended in 4 ml of 20 mM Tris-Cl (pH 8.0) with a protease inhibitor cocktail (Roche Applied Sciences, Indianapolis, Ind.). The bacteria were sonicated on ice for a 30-s pulse, followed by a 30-s rest, ten times using a Sonic Dismembrator Model 500 (Fisher Scientific) at a power of 70%. The samples were then centrifuged for 1 h at 16,000×g at 4° C. in an Eppendorf centrifuge 5415 R (Fisher Scientific). Protein concentration of the sonicate was determined by the Bradford protein assay (Bio-Rad Laboratories, Hercules, Calif.).

Fish. Adult and fingerling tilapia nilotica (*Oreochromis niloticus*) used during the trial were obtained from a source with no history of *Francisella* infection (TilTech Aquafarm, Robert, La.). For verification, a sub-sample of the population was tested for, bacteria by complete clinical, bacteriological, serological and molecular analysis to ensure that they were free of *F. asiatica*. Fingerlings were maintained at 15 fish per tank in 40 L tanks containing 30 L of water flowing through at 25° C., and fed commercial tilapia feed daily (Burris Aquaculture Feeds, Franklinton, La.) at 3% fish body weight per day. The mean weight of the fish was 6.4 g. Adults weighing an average of 346 g were acclimated for a minimum of 2 months in a flow through water system at 25° C. Five adult fish were maintained in a 100 L tanks containing 80 L of water/tank with constant oxygenation.

Immunization and challenge. Vaccination trials were conducted using tilapia fingerlings. Four different ΔiglC mutant vaccination treatments and a mock immunized control treatment were evaluated. Each treatment consisted of eight tanks (15 fish in each tank). The first group of fish was vaccinated by addition of $10^7$ CFU/ml of the ΔiglC mutant to 10 L of static water and incubation for 180 min. The second group received a dose of $10^7$ CFU/ml of the ΔiglC mutant but for 30 min. The third group received a dose of $10^3$ CFU/ml of the ΔiglC mutant for 180 min; and the fourth group received a dose of $10^3$ CFU/ml of the ΔiglC mutant for 30 mM. The control tanks received 100 ml of 1×PBS into 10 L of static water for a period of 180 mM. After either 30 or 180 min, the flowing water in each tank was restored to a final volume of 30 L of water/tank. Four weeks following a single immersion immunization with the ΔiglC mutant or PBS (control tanks), tilapia fingerlings were challenged by immersion as described above. Briefly, water volumes in each tank were adjusted to 10 L of water/tank, and 100 ml of PBS containing *F. asiatica* suspension was added to each tank for a final concentration of $10^8$ CFU/ml of WT *F. asiatica*. The fish colonization and infection was allowed to progress for 180 minutes in static water with oxygenation, after which flowing water was re-assumed to a final volume of 30 L/tank. Three tanks per treatment were utilized for monitoring mortality every 12 h for 30 days. The remaining tanks were utilized for mucus and serum collection and analysis. The protective index was calculated according to the formula as described by Aned 1981: RPS=100%(1−(% mortality in vaccinated fish/% mortality in control fish).

Mucus and serum collection. Mucus and serum collection was performed following as described by Grabowski et al. 2004. Mucus was sampled from 5 tilapia fingerlings from each immunized or mocked-immunized group at 0, 2, 4, 6, 8 and 10 weeks post-vaccination. Fish were euthanized with an overdose of MS-222 and mucus collected by swabbing both sides of the fish 10 times from head to tail with a cotton applicator. Swabs were placed in 1.5 ml microcentrifuge tubes containing 0.9 mL of PBS supplemented with 0.02% (w/v) sodium azide. Tubes were stored overnight at 4° C. The next morning, tubes and swabs were vigorously vortexed for 2 min and liquid removed from the swabs by pressing against the side of the tube. The resulting liquid was centrifuged at 3000×g for 10 min and the supernatant collected and frozen at −20° C. in polypropylene tubes until analyzed by ELISA.

For serum analyses, blood samples were obtained from the same fish at each time point by caudal venepuncture and collection with plain Fisherbrand micro-hematocrit capillary tube (Fisher Scientific, Pittsburgh, Pa.). Blood was held at 25° C. for 1 h, and then the serum separated from cells with centrifugation at 400×g for 5 min and then stored at −20° C. for later analysis by ELISA.

ELISA. An ELISA was developed to quantify anti-*F. asiatica* antibody produced by tilapia in serum and mucus. Immulon II 96-well flat-bottom microtitre plates (Thermo Labsystems, Franklin, Mass., USA) were coated overnight at 4° C. with a 7 ug protein $mL^{-1}$ solution of sonicated *F. asiatica* whole cell antigen in 0.05 M carbonate coating buffer, pH 9.6, at 100 μL per well. Plates were then washed three times in PBS containing 0.05% Tween-20 (PBST). The wells were blocked for 1 h at room temperature (RT) with filter-sterilized PBS containing 0.05% Tween 20 (Sigma) and 1% bovine serum albumin (BSA; Fraction V, Sigma) (PBST-BSA). Tilapia serum and mucus samples were diluted 1:1000 or 1:50 (respectively) in PBST-BSA, and 100 μL of the resulting solution was added to three replicate wells of the microtitre plate. The plate was incubated at 25° C. for 2 h and washed 3× with PBST. Mouse anti-tilapia IgM heavy chain specific monoclonal antibody (USDA/ARS, Auburn, Ala.) was diluted 1:100 in PBST and 100 μL of this solution added to each well as described by Shelby et al. 2002. The plate was incubated at 25° C. for 1 h and washed 3× with PBST. Peroxidase-conjugated goat anti-mouse IgG (Pierce Biotechnology, Rockford, Ill., USA) was diluted 1:10,000 in PBST and added to each well. After incubation at 25° C. for 1 h, the plate was washed again 3× in PBST and 100 μL of ABTS Peroxidase Substrate System (KPL, Gaithersburg, Md.) was added to each well. The ELISA reaction was stopped after 30 min with 100 μL 1% sodium dodecyl sulfate (SDS), and the optical density (OD) of the reactions was read at 405 nm with a SpectraMax M2/M2e Microplate Readers (Molecular Devices, Sunnyvale, Calif.). The relative amount of specific antibody was measured as the OD value.

Adoptive transfer studies. Twenty adult fish serum donors were immunized by intraperitoneal (IP) vaccination with the *F. asiatica* ΔiglC mutant. Prior to challenge the fish were anesthetized with MS-222 (100 mg/l). Intraperitoneal vaccinated fish received a 0.1 ml injection of bacterial suspension ($10^7$ CFU/fish). Serum collected from the 20 immunized fish at 4, 5, and 6 weeks post-immunizations were pooled together and was analyzed by ELISA. Endpoint titers were reported as the reciprocal of the last dilution yielding an OD more than twice that of the serum from naïve control fish. Normal fish serum was obtained from 20 adult naïve fish injected with 1×PBS and processed the same way as the immunized fish. Heat-inactivated immunized serum (HIIS) and heat-inactivated normal serum (HINS) were obtained by incubating serum obtained from immunized and mocked immunized fish at 56° C. for 30 min. Two hundred and forty naïve tilapia fingerlings (20/tank) were injected IP with either 200 μl of pooled HIIS, HINS or PBS 24 h before IP challenge with *F. asiatica* WT. Three tanks per treatment were challenged with either $10^3$, $10^4$, $10^5$, or $10^6$ CFU *F. asiatica*/fish by IP injection. During the subsequent 21-d challenge period, fish were monitored daily for clinical signs of disease and mortality. Moribund and dead fish were removed twice daily, and bacterial samples were aseptically obtained from the spleen of morbid and dead fish to confirm the presence of *F. asiatica*. The $LD_{50}$ for each treatment was calculated by the method of Reed-Muench (1938), at day 21 post-injection.

Direct Complement Lysis. *F. asiatica* WT and *E. coli* DH5a were cultured as described above. Bacteria were adjusted to a concentration of $1\times10^7$ CFU/ml in PBS. A 1:1 ratio of the bacterial isolates to either PBS, normal (NS) or immunized (IS) tilapia serum was combined, and the samples were incubated for 2 h at room temperature. Following incubation sub-samples of the bacteria/serum mixtures were collected at 0, 1, and 2 h, serially diluted in PBS, and spotted onto either CHAH (*F. asiatica*) or LB (*E. coli*) plates.

Opsonophagocytosis assays. To examine the opsonic potential of the immune sera, an opsonophagocytosis assay was established. Tilapia head-kidney derived macrophages (HKDM) were collected and purified as described in Neumann et al. 1998 and Secombes 1992. To infect tilapia HKDM, 5 day cultures of tilapia HKDM in 96 well plates containing 1-$5\times10^5$ cells/well were used. *F. asiatica* was grown for a period of 8 h in MMH at 25° C. Optical density ($OD_{600}$) of the culture was determined, and the bacteria were adjusted to a final concentration of $5\times10^8$ CFU/ml. One ml aliquots of the bacterial suspension was pelleted at 10,000×g for 5 minutes in an Eppendorf 5415 D centrifuge (Eppendorf-Brinkman, Westbury, N.Y.), and the pellet was resuspended in either 1 ml of HINS or HIIS. Ten-fold serial dilutions were plated on CHAH after incubation to determine total bacterial cell viability. After 1 h incubation, the 96 well plate was inoculated with 10 μl of opsonized bacteria per well to achieve a multiplicity of infection (MOI) of 50 bacteria: 1 macrophage. The plates were centrifuged for 5 min at 400×g to synchronize bacterial contact with macrophages. Following 2 h incubation at 25° C. with 5% $CO_2$, the cells were washed three times with warm media (25° C.), further incubated with fresh media and lysed for 15 min at time 0, 24, and 48 h by the addition of 100 of 1% Saponin in PBS. The lysates were serially diluted and spread onto CHAH plates to determine viable counts. Experiments were performed in triplicate on a minimum of three separate occasions with similar results.

Statistical Analysis. The Statistical Analysis System (SAS Institute, Inc. 2003) was used with the general linear models procedure (PROC GLM) to conduct analysis of variance (ANOVA) of a factorial arrangement of treatments. When the overall test indicated significance, pairwise comparisons of main effects were calculated with Tukey's test. Interaction effects were examined with pairwise t-test comparison of least-square means. For the mortality studies the percent mortalities were transformed with an arcsine transformation to normalize the data. To ensure overall protection level of Type I error, only probabilities associated with pre-planned comparisons were used. All comparisons were considered significant at $P<0.05$.

EXAMPLE 9

Attenuated *F. asiatica* ΔiglC Mutant Induced Protective Immunity

Figure 6:
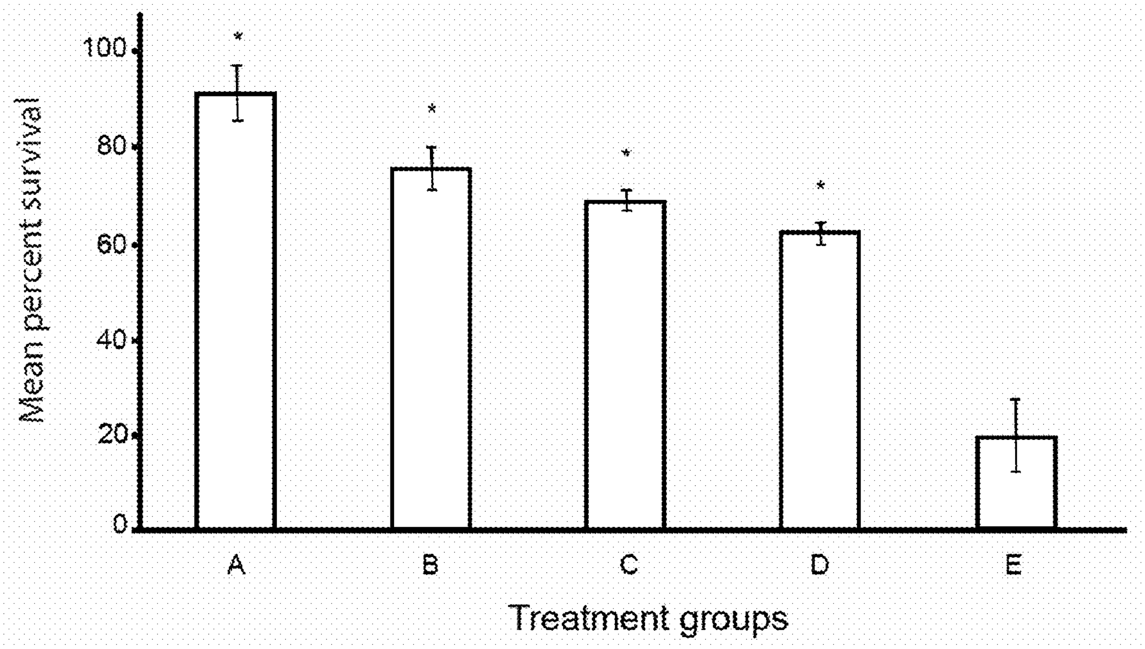
FIG. 6 illustrates the mean percent survival of tilapia vaccinated with different treatments of *Francisella asiatica* ΔiglC mutant by immersion, or mock vaccinated with PBS (Controls) and challenged 4 weeks later with WT *F. asiatica*. Fish were vaccinated with: A. $10^7$ CFU/ml of the *F. asiatica* ΔiglC mutant for 180 min. B. $10^7$ CFU/ml of the *F. asiatica* ΔiglC mutant for 30 min. C. $10^3$ CFU/ml of the *F. asiatica* ΔiglC mutant for 180 min. D. $10^3$ CFU/ml of the *F. asiatica* ΔiglC mutant for 30 min. E. PBS for 180 min. Four weeks post-immunization fish were challenged with $10^8$ CFU/ml of WT *F. asiatica* for 180 min. Mean percent survival was calculated 30 days post-challenge with WT. Each bar represents the mean percent survival±standard error of three tanks (15 fish/tank). *Denotes significant differences, $P<0.05$ with respect to the control group by a Student's t-test.

Part 2—Immersion Vaccination with ΔiglC Protected Tilapia Fingerlings Against Homologous *F. asiatica* Immersion Challenge To evaluate the efficacy of the *F. asiatica* ΔiglC mutant in protecting tilapia fingerlings against virulent *F. asiatica* immersion challenge, tilapia fingerlings were vaccinated by immersion by four different treatments. Vaccination with a dose of $10^7$ CFU/ml of water for a period of 30 or 180 min conferred 68.75% and 87.5% relative percent survival (RPS) respectively, against otherwise lethal (80% mortality) immersion challenge with the wild-type (WT) isolate during a period of 30 days. FIG. 6 shows the mean percent survival of tilapia vaccinated with different treatments of *F. asiatica* ΔiglC mutant by immersion, or mock vaccinated with PBS (Controls) and challenged 4 weeks later with WT *F. asiatica*. Fish were vaccinated with: A. $10^7$ CFU/ml of the ΔiglC mutant for 180 min. B. $10^7$ CFU/ml of the ΔiglC mutant for 30 min. C. $10^3$ CFU/ml of the ΔiglC mutant for 180 min. D. $10^3$ CFU/ml of the ΔiglC mutant for 30 min. E. PBS for 180 min. Four weeks post-immunization fish were challenged with $10^8$ CFU/ml of WT *F. asiatica* for 180 min. Mean percent survival for FIG. 6 was calculated 30 days post-challenge with WT. Each bar represents the mean percent survival±standard error of three tanks (15 fish/tank). An "*" Denotes significant differences, $P<0.05$ with respect to the control group by a Student's t-test.

As shown in FIG. 6, vaccination with a dose of $10^3$ CFU/ml of water for a period of 30 min or 180 min conferred 56.25% and 62.5 RPS respectively, against immersion challenge with the WT isolate. Mock (PBS)-vaccinated fish succumbed to the infection by day 7, presenting clinical signs of the disease, including ascites and widespread granulomas in spleen and kidney. Fish vaccinated with either treatments of ΔiglC mutant had significantly higher survival rates than those mocked vaccinated with PBS after challenge with WT *F. asiatica* ($p<0.05$) (FIG. 6).

Figure 7:
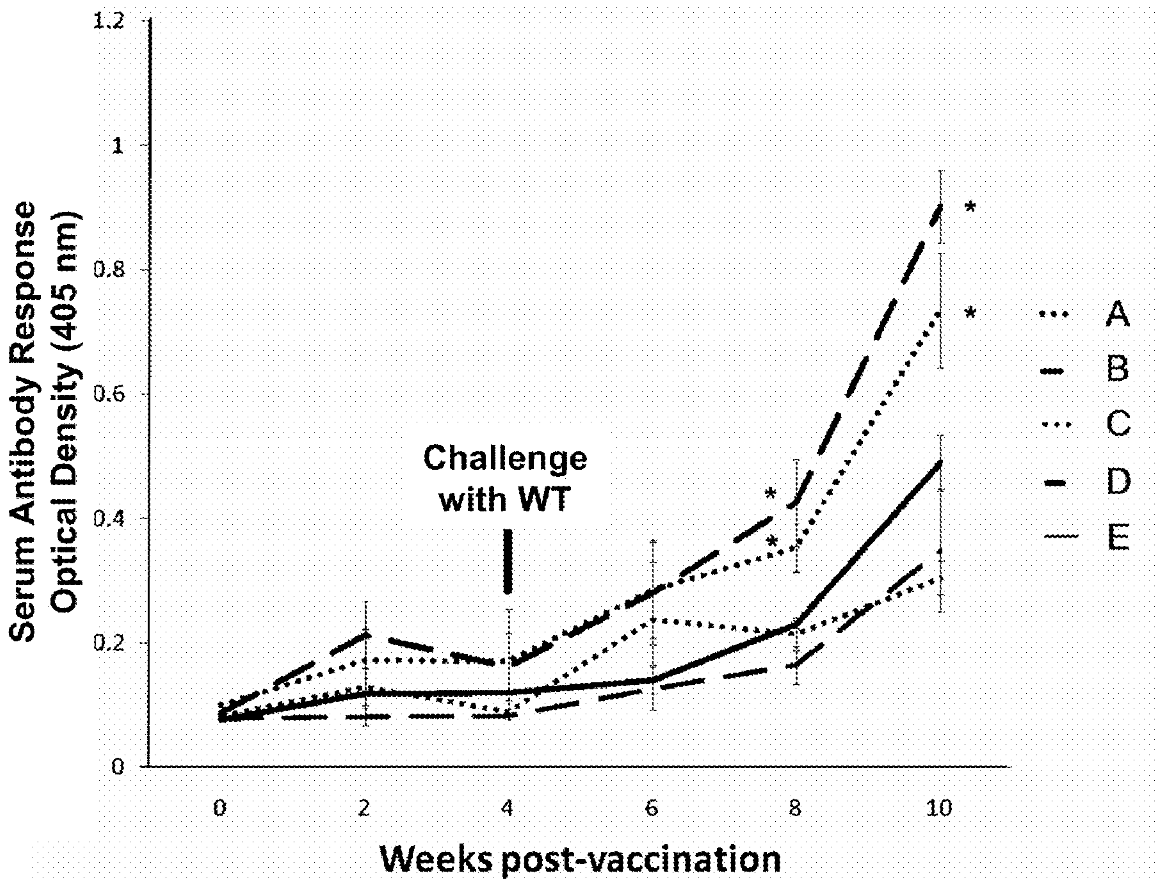
FIG. 7 illustrates the serum anti-*F. asiatica* antibody response in actively immunized tilapia fingerlings. Fish were vaccinated with: A. $10^7$ CFU/ml of the *F. asiatica* ΔiglC mutant for 180 min. B. $10^7$ CFU/ml of the *F. asiatica* ΔiglC mutant for 30 min. C. $10^3$ CFU/ml of the *F. asiatica* ΔiglC mutant for 180 min. D. $10^3$ CFU/ml of the *F. asiatica* ΔiglC mutant for 30 min. E. PBS for 180 min. Four weeks post-immunization fish were challenged with $10^8$ CFU/ml of WT *F. asiatica* for 180 min. Each point represents the mean OD value±standard error of 5 fish samples (serum). *Denotes significant differences, $P<0.05$ with respect to the control group by a Student's t-test.

FIG. 7 shows the serum anti-*F. asiatica* antibody response in actively immunized tilapia fingerlings. Fish were vaccinated with on of the following: A. $10^7$ CFU/ml of the ΔiglC mutant for 180 min. B. $10^7$ CFU/ml of the ΔiglC mutant for 30 min. C. $10^3$ CFU/ml of the ΔiglC mutant for 180 min. D. $10^3$ CFU/ml of the ΔiglC mutant for 30 min. E. PBS for 180 min. At four weeks post-immunization, fish were challenged with $10^8$ CFU/ml of WT *F. asiatica* for 180 min. Antibodies were measured during 10 weeks post-vaccination (every 2 weeks) as described above. Serum was diluted 1:1000. Mean OD values were calculated for each treatment every two weeks. Each point represents the mean OD value±standard error of 5 fish samples (serum). * Denotes significant differences, $P<0.05$ with respect to the control group by a Student's t-test.

Figure 8:
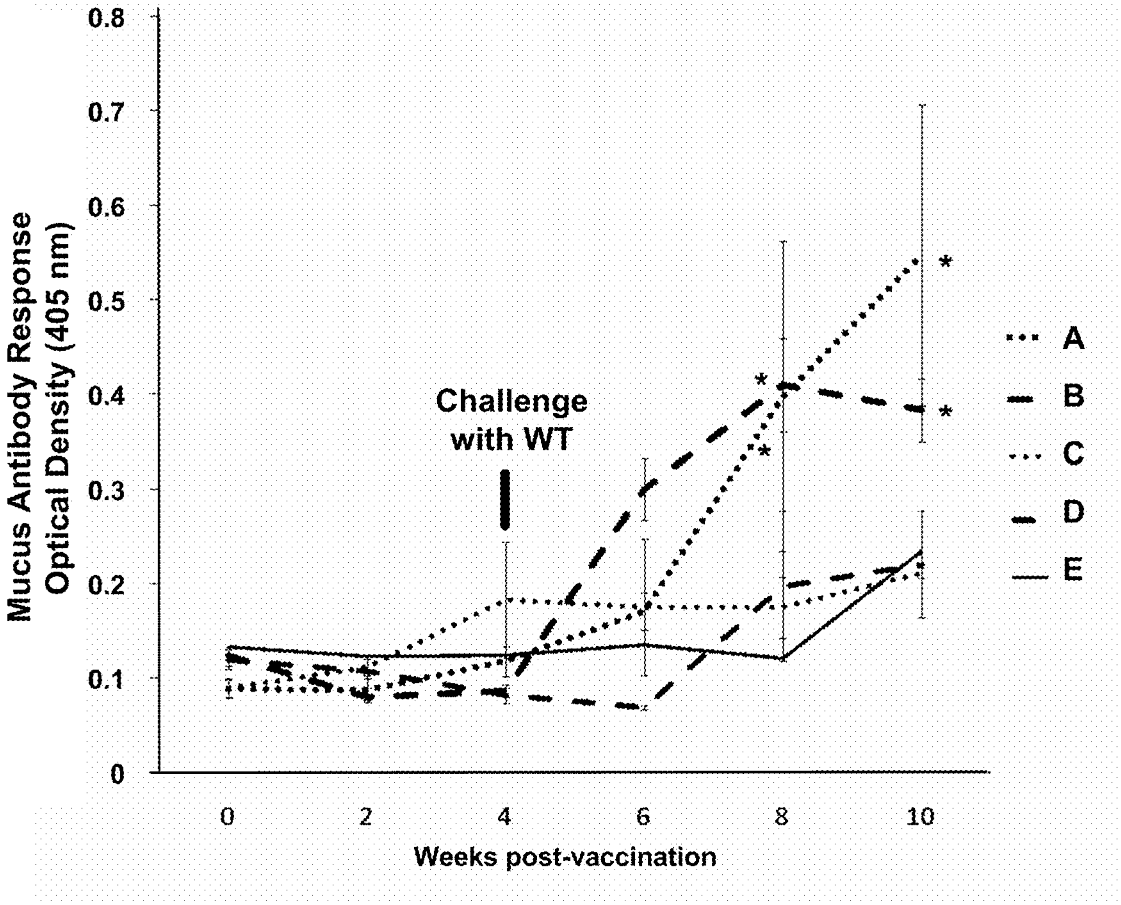
FIG. 8 illustrates the mucus anti-*F. asiatica* antibody response in actively immunized tilapia fingerlings. Fish were vaccinated with: A. $10^7$ CFU/ml of the *F. asiatica* ΔiglC mutant for 180 min. B. $10^7$ CFU/ml of the *F. asiatica* ΔiglC mutant for 30 min. C. $10^3$ CFU/ml of the *F. asiatica* ΔiglC mutant for 180 min. D. $10^3$ CFU/ml of the *F. asiatica* ΔiglC mutant for 30 min. E. PBS for 180 min. Four weeks post-immunization fish were challenged with $10^8$ CFU/ml of WT *F. asiatica* for 180 min. Each point represents the mean OD value±standard error of 5 fish samples (mucus). * Denotes significant differences, $P<0.05$ with respect to the control group by a Student's t-test.

FIG. 8 shows the mucus anti-*F. asiatica* antibody response in actively immunized tilapia fingerlings. Fish were vaccinated with: A. $10^7$ CFU/ml of the ΔiglC mutant for 180 min. B. $10^7$ CFU/ml of the ΔiglC mutant for 30 min. C. $10^3$ CFU/ml of the ΔiglC mutant for 180 min. D. $10^3$ CFU/ml of the ΔiglC mutant for 30 min. E. PBS for 180 min. Four weeks post-immunization fish were challenged with $10^8$ CFU/ml of WT *F. asiatica* for 180 min. Antibodies were measured during 10 weeks post-vaccination (every 2 weeks) as described above. Mucus was diluted 1:50. Mean OD values were calculated for each treatment every two weeks. Each point represents the mean OD value±standard error of 5 fish samples (mucus). *Denotes significant differences, $P<0.05$ with respect to the control group by a Student's t-test.

As shown in FIGS. 7 and 8, juvenile tilapia vaccinated with either treatment of ΔiglC mutant generated a weak serum and mucosal antibody response that wasn't significantly different than that of controls at 2, 4 and 6 weeks post-vaccination. However, after the WT immersion challenge, the serum and mucosal samples from ΔiglC mutant vaccinated fish with a dose of $10^7$ CFU/ml of water for a period of 30 and 180 min, resulted in a significantly greater secondary antibody response at week 8 and 10 post-initial vaccination ($p<0.05$) (FIG. 7, FIG. 8). The non-immunized fish showed an increased primary antibody response after WT challenge when compared to antibodies levels at week 0 (FIGS. 7 and 8).

EXAMPLE 10

Attenuated *F. asiatica* ΔIglC Mutant Induced Protective Immunity

Part 2—Antibodies Partially Contribute to the Protection Conferred by Vaccination with the *F. asiatica* ΔIglC Mutant Intraperitoneal injection with the *F. asiatica* ΔiglC mutant induced a strong humoral response in adult tilapia and enhanced the production of antibodies. The pooled immunized sera presented antibody titers >52,000. To test the functional ability of such antibodies, opsonophagocitic and killing assays were performed, as well as passive immunization trials.

*F. asiatica* susceptibility to direct effects of IS was compared with that of *E. coli*, after mixing the bacteria strains with PBS, normal serum (NS) or immunized serum (IS) for a period of 2 h. Both IS and NS completely inhibited growth of the *E. coli* isolate. In contrast, neither IS or NS had an effect on the growth of *F. asiatica* in vitro (data not shown).

Figure 9:
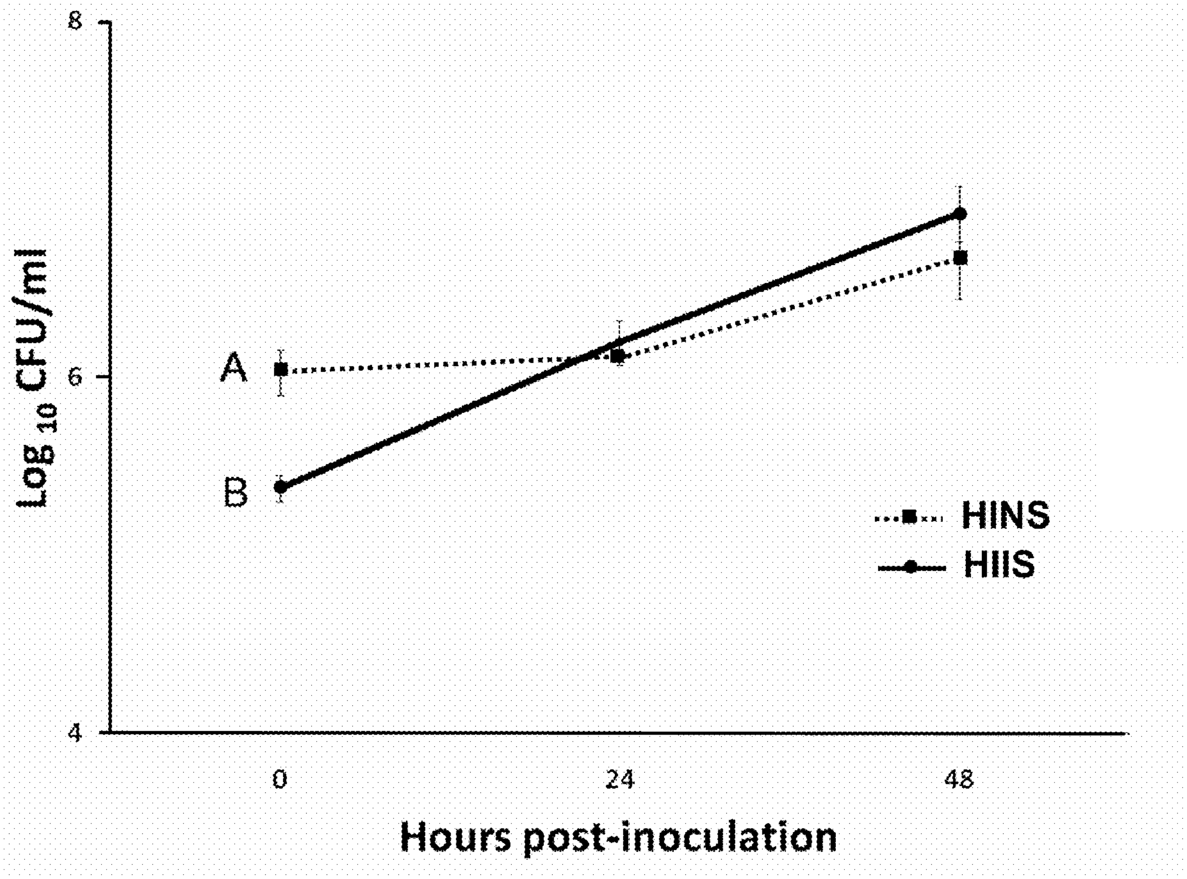
FIG. 9 illustrates the enhanced antibody-dependent phagocytosis of *F. asiatica* by tilapia head kidney derived macrophages (HKDM). *F. asiatica* was opsonized with heat-inactivated immunized (HIIS) or heat-inactivated normal (HINS) sera obtained from adult tilapia. Results are shown as mean $Log_{10}$ CFU/ml of *F. asiatica* uptake in HKDM at 0, 24, and 48 h time point. The error bars represent standard error of triplicate samples and the results shown are representative of three independent experiments. Different letters denote significant differences between treatments, $P<0.05$.

To test the functional ability of antibodies against *F. asiatica* in the heat-inactivated immunized serum (HIIS) to mediate phagocytic uptake of *F. asiatica* WT, a complement-independent opsonophagocytic assay using tilapia head kidney derived macrophages (HKDM) was utilized. FIG. 9 shows the enhanced antibody-dependent phagocytosis of *F. asiatica* by HKDM. *F. asiatica* was opsonized with heat-inactivated immunized (HIIS) or heat-inactivated normal (HINS) sera obtained from adult tilapia. Phagocytosis assays were performed with tilapia HKDM (MOI 1:50) as described above. Results are shown as mean $Log_{10}$, CFU/ml of *F. asi-*

*atica* uptake in HKDM at 0, 24, and 48 h time point. The error bars represent standard error of triplicate samples, and the results shown are representative of three independent experiments. Different letters denote significant differences between treatments, $P<0.05$. (FIG. 9). Heat-inactivated sera prepared from tilapia immunized with the ΔiglC mutant efficiently mediated phagocytosis of the WT *F. asiatica*, whereas HINS opsonophagocytosis ability was significantly lower ($p<0.05$). Bacteria taken up by the HKDM efficiently grew regardless of being opsonized or not with antibodies (FIG. 9).

Figure 10:
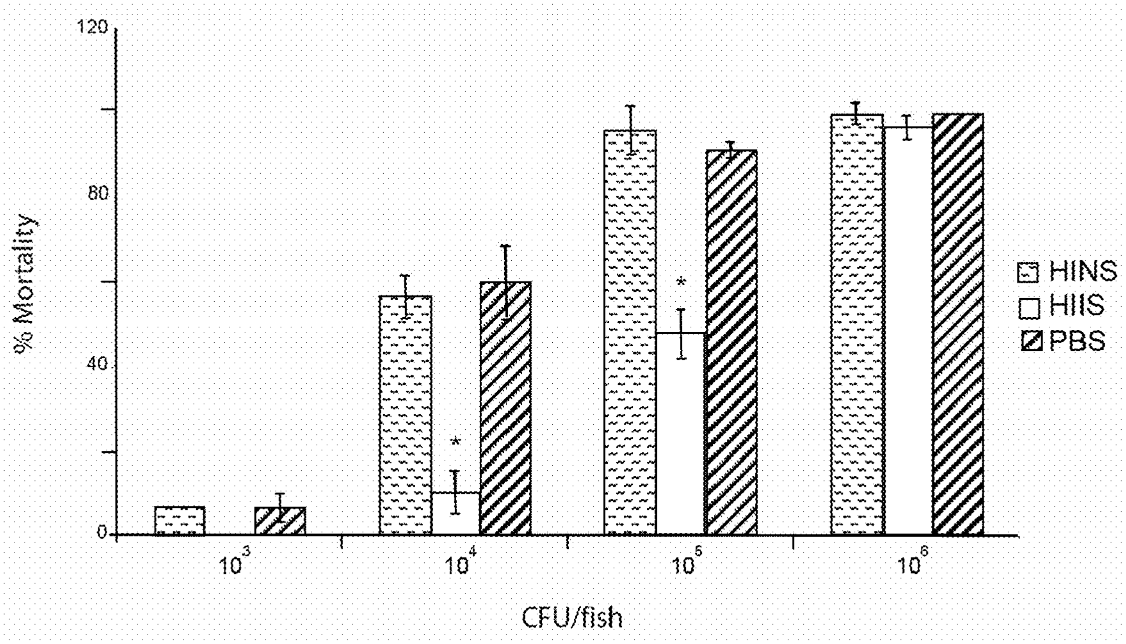
FIG. 10 illustrates the adoptive transfer of heat-inactivated normal serum (HINS), heat-inactivated immunized serum (HIIS) or PBS to naïve tilapia fingerlings. Mean percent mortality for each treatment was calculated 21 days post-challenge with wild type. Each bar represents the mean percent mortality±standard error of three tanks (20 fish/tank). *Denotes significant differences, $P<0.05$ with respect to the control group (PBS) by a Student's t-test.

Due to the strong antibody response observed in immunized fish, a series of passive transfer experiments were performed to determine whether these antibodies could prevent infection in vivo. Naive tilapia fingerlings received IP injections of PBS, HINS or HIIS sera (200 μL) collected from adult tilapia immunized with $10^7$ CFU/fish. The tilapia fingerlings were then challenged (IP) with either $10^3$, $10^4$, $10^5$ or $10^6$ CFU/fish of WT *F. asiatica* and were monitored daily for health and survival for a total of 21 days post challenge. FIG. 10 shows the adoptive transfer of heat-inactivated normal serum (HINS), heat-inactivated immunized serum (HIIS) or PBS to naïve tilapia fingerlings. Immune sera was collected from 20 adult tilapia vaccinated by intra-peritoneal injection (IP) with the ΔiglC mutant 4, 5 and 6 weeks post-vaccination. Sera were pooled, and antibodies titers were measured before passively immunized the fingerlings. Normal sera were collected and pooled form 20 adult tilapia injected with PBS 4, 5 and 6 weeks post-injection. Naïve fingerlings (60 fish/treatment) were injected IP with 200 μl of pooled HINS, HIIS or PBS 24 h before IP challenge with $10^3$, $10^4$, $10^5$ or $10^6$ CFU/fish of *F. asiatica* WT. Animals were monitored daily for morbidity and mortality. Results are representative of two independent experiments. Mean percent mortality for each treatment was calculated 21 days post-challenge with WT. Each bar represents the mean percent mortality±standard error of three tanks (20 fish/tank). *Denotes significant differences, $P<0.05$ with respect to the control group (PBS) by a Student's t-test.

Although passive immunization of HIIS did not protect'against high doses of the bacterium ($10^6$ CFU/fish) injected in the peritoneum of naïve fingerlings, significant ($p<0.05$) reductions in mortality were observed in HIIS immunized fish when challenged to $10^4$ and $10^5$ CFU/fish and compared to those immunized with PBS or HINS (FIG. 10).

A live attenuated vaccine given to the fish by the immersion route has the advantage of directly targeting the natural routes of attachment and penetration of the bacteria into the fish and hence inducing protective immunity at the primary site of infection. Results showed that an immersion vaccination with four different treatments of a ΔiglC mutant significantly ($p<0.05$) protected tilapia fingerlings against homologous *F. asiatica* immersion challenge (FIG. 6). Results of immunization trials indicated that when the ΔiglC mutant vaccine was delivered for either 30 or 180 m at a dose of $10^7$ CFU/ml, relative percent survival (RPS) values of 68.75% and 87.5% were obtained, demonstrating the potential of the vaccine to prevent francisellosis in tilapia. During the first 4 weeks post-vaccination, a relatively small antibody response was observed in immunized fish, and they weren't significantly different to those observed in the control groups. However, upon exposure to WT *F. asiatica*, a significantly higher ($p<0.05$) mucosal and humoral antibody response was evident in the fish vaccinated with a dose of $10^7$ CFU/ml (FIG. 7, FIG. 8).

The passive immunity studies described here demonstrate that *F. asiatica*-specific antibodies mediate protection after IP injection of different concentration of *F. asiatica* WT (FIG. 10). Thus the *F. asiatica*-specific antibody response is a useful component of the protective immune response to lethal *F. asiatica* infection in fish. Since *F. asiatica* is a facultative intracellular organism, the bacteria can exist in an extracellular form in the tilapia, and thus the antibodies may be able to prevent the systemic spread of bacteria.

An attenuated strain of *F. asiatica* (ΔiglC mutant) was discovered as a live-vaccine to protect fish from francisellosis, especially *F. asiatica*. Immunization of tilapia nilotica with the ΔiglC mutant by immersion delivery provided long lasting protective immune responses ($p<0.05$), as demonstrated by antibodies levels, and the antibodies directed to *F. asiatica* were protective as shown in passive immunity trials. Without wishing to be bound by this theory, based on the homology among *Francisella* spp. of the iglC gene, we believe that this attenuated strain of *F. asiatica* (ΔiglC) could be used to provoke an immune response in fish other than tilapia to protect from infection by *F. asiatica*, for example, tilapia hybrids, hybrid striped bass and three line grunt. In addition, based on the similarity of the fish *Francisella* spp. in general, we believe that vaccination with the *F. asiatica* ΔiglC mutant could provide at least some immunity against infection from any fish *Francisella* pathogen, e.g., *F. noatunensis*.

EXAMPLE 11

Live-Attenuated *F. asiatica* as Vectors of Heterologous Antigens

In addition, this *F. asiatica* ΔiglC mutant may be used not only to vaccinate fish against *Francisella*, but also to serve as a vector to present antigens from other pathogens to the fish immune system, therefore serving as vaccines against other known pathogens of fish as well. Because attenuated *F. asiatica* retains its invasive properties and can be administered by immersion, this attenuated strain is an ideal candidate to use as a vector for delivering heterologous antigens for vaccination. The genetic manipulation techniques have been established for attenuated *Salmonella* strains. The same general techniques will be used here. A number of different genes from viruses, bacteria and parasites have been successfully expressed in attenuated *Salmonella* and the recombinant strains used to immunize small animals. See review in Roberts et al. (1994), and Kang et al. 2002.

Briefly the same techniques as described above will be used to create iglC mutations where the inserted sequences contain both the kanamycin resistance gene to facilitate selection (or another selection marker) and also a gene encoding the heterologous antigen. Preferably the gene for the heterologous antigen is placed under the control of the native promoter for the iglC gene or the promoter for the selection marker to ensure the antigen is expressed and is seen by the fish immune system before it is cleared.

These vaccines are preferably administered to relatively young fish raised in a specific pathogen free environment so the fish will have no pre-existing immunity to the wild type of the carrier strain. Such pre-existing immunity could cause the carrier strain to be cleared too quickly.

Heterologous antigens would be selected from those found in other important tilapia pathogens, *Streptococcus agalactiae* and *S. iniae*. Examples of heterologous antigens from *S. agalactiae* would be the surface immunogenic protein sipA, the cell surface associated protein cspA, and the components of the general protein secretion pathway secY. The antigens from *S. iniae* would be the hemolysins and M proteins. Currently there are no important virus diseases of cultured tilapia.

EXAMPLE 12

Assay for Specific Identification of *Francisella asiatica*

Bacterial Strains. The bacterial strains used in this project were chosen because they represent common bacterial fish pathogens, or are members of the genus *Francisella*. Strain *F. asiatica* LADL 07-285A, isolated from diseased cultured tilapia (*Oreochromis* spp.) was chosen as a representative of the warm water strain of fish pathogenic *F. asiatica*. The majority of the isolates tested were recovered by the Louisiana State University, School of Veterinary Medicine (LSU-SVM), Louisiana Aquatic Diagnostic Laboratory (LADL), from diseased fish, while others were acquired from the American Type Culture Collection (ATCC). *Francisella tularensis* subsp. *novicida* U112 and *F. tularensis* subsp. *holarctica* (LVS isolate) DNA were obtained from the Department of Biology, University of Texas, San Antonio, Tex. *Francisella noatunensis* subsp. *noatunensis* is a recently described member of the genus *Francisella* isolated from farmed Atlantic cod (Mikalsen et al. 2007; Ottem et al. 2009; Mikalsen & Colquhoun 2009), and was obtained from National Veterinary Institute, Bergen, Norway. *Francisella* isolates #1, #2, and #3 recovered from moribund hybrid striped bass (Ostland et al. 2006) and *F. victoria* recovered from tilapia (Kay et al. 2006) and showing >99% identity with *F. noatunensis* subsp. *orientalis* after 16S rDNA sequence comparison, were obtained from the University of Washington, Seattle, Wash. *Francisella asiatica* LADL 07-285A was grown in cystine heart agar with hemoglobin (CHAH) supplemented as outlined in Soto et al. 2009a, for 48 h at 28° C. *Francisella noatunensis* subsp. *noatunensis* was grown in a similar manner but was incubated at 20° C. for 5 d. *Flavobacterium columnare* was grown on dilute Mueller Hinton agar for 48 h at 28° C. *Mycobacterium marinum* and *Nocardia seriolae* were grown on Lowenstein Jensen slants for one week at 28° C. All the other bacteria used in the study were grown on blood agar (BA) 5% sheep blood plates for 48 h at 28° C.

Template DNA Preparation. Bacterial cultures grown on agar media were suspended in 1 ml of 1× phosphate buffered saline (PBS) and 200 μl was used for nucleic acid isolation following the manufacturer's protocol in the High Pure PCR Template Preparation Kit (Roche Diagnostics, Mannheim, Germany). Nucleic acid was also extracted from a negative control consisting of 1× sterile PBS alongside of the unknowns to ensure no cross-contamination occurred during the extractions.

TagMan Primers and Probe. The TaqMan primers and probe used in this study were designed based on the nucleotide sequence comparison of the iglC gene of *F. tularensis* subsp. *novicida* U112 iglC (GeneBank Accession number AY293579), *F. tularensis* subsp. *holarctica* FTNF002-00 (GeneBank Accession number CP000803) iglC, *F. tularensis* subsp. *mediasiatica* FSC 147 iglC (GeneBank Accession number CP000915), *F. philomiragia* ATCC 25017 iglC (GeneBank Accession number CP000937), and *F. noatunensis* subsp. *orientalis* LADL 07-285A iglC (GeneBank Accession number FJ386388) (Table 3). The primers and probe were designed following the real-time qPCR Assay Design Software (Biosearch Technologies, San Francisco, Calif., USA). Primers and probe concentration were optimized at the beginning to determine the minimum primer concentrations giving the maximum ΔRn, and the minimum probe concentration that gave the minimum $C_T$. The optimization was done according to the TaqMan Universal PCR Master Mix manufacturer (Applied Biosystems, Foster City, Calif., USA).

TABLE 3

TaqMan primers and probe used in this study

| Primers and Probes | 5′-3′ Sequence | Melting temperature (C°) |
|---|---|---|
| iglC forward | Gggcgtatctaaggatggtatgag (SEQ ID NO: 21) | 66.36 |
| iglC reverse | Agcacagcatacaggcaagcta (SEQ ID NO: 22) | 66.63 |
| iglC probe | FAM atctattgatgggctcacaacttcacaa BHQ-1 (SEQ ID NO: 23) | 68.34 |

Real-time TagMan PCR Assays. The real-time PCR assays were conducted and analyzed within the Applied Biosystems 7500 Fast Real-Time PCR Systems (Applied Biosystems). The 25 μl reaction mixture consisted of a TaqMan Universal PCR Master Mix (Applied Biosystems), containing 10 μmol of each primer, 3 μmol of probe and 5 μl of DNA extracted sample. Template controls containing PCR grade water and seven serial dilutions of 100 ng $\mu l^{-1}$ of *F. asiatica* isolate LADL 07-285A diluted in PCR grade water and measured in a NanoDrop Spectrophotometer ND-V3.5 (Nanoprop Technologies Inc., Wilmington, Del.) were included in each run. The unknown samples, as well as the diluted standards and negative controls were run in triplicate. Cycling conditions were 2 min at 50° C., 15 min at 95° C. followed by 40 cycles of 15 s at 95° C., 60 s at 60° C.

The assay was found to be specific for the warm water fish pathogen, *F. asiatica* and no evidence of crossreactivity was detected (no significant elevated signal was observed with any of the other tested bacterial DNA) (Data not shown).

Sensitivity of the Real Time PCR Assays. For sensitivity determination, the TaqMan assays were evaluated by two different independent methods. Three separate extractions of *F. asiatica* DNA were adjusted to a concentration of 100 ng $\mu l^{-1}$ Nanoprop Spectrophotometer ND-1000V3.5 (Nanodrop Technologies Inc., USA), and ten fold dilutions were made in PCR grade water until reaching a concentration of 1 fg $\mu l^{-1}$. Genome equivalent (GE) calculation was based on assuming a 2-MB genome size for *F. philomiragia* and several subspecies of *F. tularensis*. For determination of colony forming units (CFU), several isolated colonies of *F. asiatica* were picked from a fresh CHAH culture and suspended in 1 ml of phosphate buffered saline (PBS) pH 7.2, until an $OD_{600}$ of 0.75 was reached and measured in a DU-640 Spectrophotometer (Beckman Coulter Inc., Brea, Calif., USA). Ten fold serial dilutions in PBS were made from this sample, and colony counts were performed on CHAH by the drop plate method to verify bacterial numbers. Extraction of DNA from 200 μl of each dilution was used for CFU quantification in the real time PCR assay. Amplification efficiencies were determined and all assays were run in triplicate.

Sensitivity of the Real Time PCR Assay in Fish Spleen. In order to determine the sensitivity limit of the assay, triplicate samples of one gram of uninfected tilapia spleen (recently acquired fresh tissue) were homogenized with a Kontes PELLET PESTLE® Micro Grinder (A. Daigger and Company Inc., 620 Lakeview Parkway, Vernon Hills, Ill., USA) in a 4 ml suspension of early stationary phase *F. asiatica* cells diluted in PBS to a final concentration of 2, 20, 200, $2\times10^3$, $2\times10^4$, $2\times10^5$, $2\times10^6$, $2\times10^7$ CFU g $tissue^{-1}$. Two hundred microliters of the homogenates containing approximately 50 mg of spleen, were centrifuged at 12 000 g for 1 min and DNA extracted following the manufacturers protocol "Isolation of Nucleic Acids from Mammalian Tissue", High Pure PCR Template Preparation Kit (Roche Diagnostics, Mannheim, Germany): Enumeration of *F. asiatica* by real-time PCR was compared with plate count values, taking into account dilution/concentration factors due to volumes used in DNA extraction and final elution volumes. Amplification efficiencies were determined and all assays were run in triplicate.

The sensitivity of the assay was determined using a triplicate dilution series from 0.5 fg $reaction^{-1}$ to 1.4 mg $reaction^{-1}$ of *F. asiatica* genomic DNA. The lowest amount of detection was determined to be 50 fg of DNA (equivalent to ~25 GE). Threshold cycle (Ct) determined by TaqMan real-time PCR amplification of DNA, extracted from serial dilutions of pure *F. asiatica* bacterial culture, showed a linear ($R^2$=0.994) relationship with log numbers of CFU from $2.5\times10^7$ to $2.5\times10^1$ CFU $ml^{-1}$ based on plate counts (Data not shown). Ten fold serial dilutions of nucleic acid extracted from the initial dilutions of the pure bacterial culture also showed a linear relationship between the log amount of nucleic acid and the TaqMan real-time PCR Ct from 1.4 mg to 50 fg. Linear detection of amplified product was also revealed in serially diluted *F. asiatica* spiked spleen homogenates ($R^2$=0.985) (Data not shown). This indicates that the presence of tissue homogenate did not impede the sensitivity of the real-time PCR assay within this range of CFUs. Uninfected tilapia spleen and water controls showed no signal after 40 cycles.

Experimental Infectivity Trial. The tilapia fingerlings used during the trial were obtained from a source with no history of *Francisella* infection and a sub-sample of the population was confirmed as negative for *Francisella* bacteria by complete clinical, bacteriological and molecular analysis as described in Soto et al. 2009a. Fish were maintained at 10 fish per tank and fed commercial tilapia feed daily (Burris Aquaculture Feeds, Franklinton, La.) at ~3% fish body weight per day. The mean weight of the fish was 9.1 g and the mean length was 18 cm. Three tanks were used per treatment, and one tank was used as a control. Fish were immersed in 8 L of static water containing approximately $3.7\times10^7$ CFU/ml in tank water for 3 h at 23-25° C., and then the volume of the tanks was adjusted to 20 liters with clean oxygenated water. Control fish were treated in a similar manner, but received sterile PBS.

Following each challenge exposure, mortality was recorded every 12 h for 30 d. Prior to collection of spleen, moribund and survivor fish were euthanized with an overdose of MS-222. The spleens from dead, moribund and survivor fish were collected aseptically in 1.5 microcentrifuge tubes (Fisherbrand, Fisher Scientific, USA), weighed, and DNA was extracted from ~20 mg of spleen following the manufacturers protocol "Isolation of Nucleic Acids from Mammalian Tissue", High Pure PCR Template Preparation Kit (Roche Diagnostics, Mannheim, Germany). The rest of the tissue was homogenized in ~50 μl PBS and plated on CHAH. The eluted DNA was stored at 4° C. until used.

At 30 days following challenge, the mean mortality in the tanks was 56.6%. In order to test the ability of the iglC TaqMan assays to identify *F. asiatica* in tilapia tissue, spleens from infected fish were analyzed. One hundred percent of the morbid and survivor (challenged) fish were positive by the assay, and all non-challenged fish were negative. Detection of the bacteria by culture on CHAH agar media was possible in 58% of the dead fish, and in 38% of the survivors. The mean amount of *F. asiatica* GE detected in spleens from dead fish analyzed by real time PCR was $1.8\times10^5$ GE $mg^{-1}$ of spleen tissue, while surviving fish presented a mean amount of $1.5\times10^3$ GE $mg^{-1}$ of spleen tissue.

A TagMan real-time quantitative PCR assay for the rapid identification and quantification of the emergent fish pathogen *F. asiatica* was thus developed. The development of this highly sensitive diagnostic method will enhance the diagnosis of this fastidious organism that could be present at low levels in fish tissue. The assay developed in this study is directed against the previously identified iglC gene in *F. asiatica* isolate LADL 07-285A. The specificity of the TaqMan probe real-time iglC PCR assay was assessed with other strains of the genus *Francisella* (*F. tularensis* subsp. *novicida* U112 and *F. tularensis* subsp. *holarctica* LVS), clinically relevant cold and warm water fish pathogens (*F. noatunensis* subsp. *noatunensis, Streptococcus* spp., *Edwardsiella* spp., *Aeromonas* spp., *Vibrio* spp., *Mycobacterium* spp., *Photobacterium* spp., etc), and non-infected tilapia splenic tissue. After 40 cycles, DNA samples from these strains failed to show amplification using the real time PCR assay, and the assay showed no cross reaction of the chosen primers and probe with fish tissue or opportunistic fish pathogens listed above. This is particularly important with francisellosis since moribund and dead fish are commonly found with secondary infections, and attempts to isolate *Francisella* spp. can be very difficult due to the fastidious nature of the organism. The high specificity achieved by the TaqMan real time PCR assay did not amplify the closely related cold water pathogen *F. noatunensis* subsp. *noatunensis*, but it did amplify representative *F. asiatica* isolates recovered from warm water cultured tilapia and striped bass.

The sensitivity limit of the assay was found to be ~50 fg of DNA (equivalent to ~25 GE or CFU) of *F. asiatica*. Different approaches were used to verify that our DNA extraction methodology and the real time PCR assay did not interfere with the results obtained in the assay. After suspending viable live bacteria in tilapia tissue homogenates and in PBS, performing CFU counts in CHAH, extracting the DNA under the same conditions, and running the assay, it was found that fish tissue did not negatively affect the real-time PCR detection or quantification of *F. asiatica*.

When experimentally infected, tilapia were used to simulate wild epizootics, the real-time PCR assay enabled detection of the bacterium in all the dead, moribund and surviving fish 30 days post challenge, whereas it was possible to isolate the bacteria by conventional culturing on agar plates in only 58.8% (10 of 17) of dead and moribund fish, and in 38% (5 of 13) of the survivor fish after 30 days post challenge. The real-time PCR assay was also able to detect the presence of *F. asiatica* in the water of infected fish by filtering the water and extracting DNA from the filter for use in the real-time PCR assay.

Thus an iglC based TaqMan real-time PCR assay was developed with high sensitivity and specificity for the detection and quantification of the emergent warm water fish pathogen *F. asiatica*. The assay can be used not only as a rapid diagnostic test for francisellosis, but can also be used as a research tool for bacterial persistence, drug therapy efficacy, epidemiological studies, screening of broodstock fish, and detection of reservoirs for infection.

As used in the Claims, "tilapia" is used as a generic term to designate fish members of the three known genera of tilapia, *Tilapia, Sarotherodon*, and *Oreochromis*, including hybrids among the species. For example, the term would encompass the Nile tilapia (*Oreochromis niloticus*), and the hybrid red tilapia, *Oreochromis mossambicus* x *O. niloticus*.

As used in the Claims, a "protective amount" of an attenuated bacterium is an amount that, when administered to a fish as a vaccine, induces a degree of immunity sufficient to reduce to a statistically significant degree the susceptibility of the fish to an infection by a pathogen, in this case, to species of the genus *Francisella.*

REFERENCES

Abd, H., T. Johansson, I. Golovliov, G. Sandstrom, and M. Forsman. 2003. Survival and growth of *Francisella tularensis* in *Acanthamoeba castellanii*. Applied and Environmental Microbiology 69:600-606.

Abril C, Nimmervoll H, Pilo P, Brodard I, Korczak B, Markus S, Miserez R, Frey J (2008) Rapid diagnosis and quantification of *Francisella tularensis* in organs of naturally infected common squirrel monkeys (*Saimiri sciureus*). Vet. Microbiol. 127:203-208

Allen, L. A. 2003. Mechanisms of pathogenesis: evasion of killing by polymorphonuclear leukocytes. Microbes and Infection 5:1329-1335.

Anderson, D. P. 1984. Fish Immunology. Pages 110-113 In: S. Zhang, and D. Hua editors. Fish Immunology. China Agriculture Press, Beijing, China.

Aned D F. 1981. Potency testing of fish vaccines. In: Anderson D P, Hennessen H, editors. Fish biologics: serodiagnostics and vaccines. Developments in biological standardization. Basel; Karger; 447-54.

Baker C N, Hollis D G, Thornsberry C. 1985. Antimicrobial susceptibility testing of *Francisella tularensis* with a modified mueller-hinton broth. J Clin Microbiol; 22(2):212-5.

Balcazar J L, Vendrell D, de B, I, Ruiz-Zarzuela I, Girones 0, Muzquiz J L (2007) Quantitative detection of *Aeromonas salmonicida* in fish tissue by real-time PCR using self-quenched, fluorogenic primers. J. Med. Microbiol. 56:323-328

Barker, J. R., and K. E. Klose. 2007. Molecular and genetic basis of pathogenesis in *Francisella tularensis*. Annals of the New York Academy of Sciences 1105:138-159.

Baron, G. S., and F. E. Nano. 1998. Mg1A and Mg1B are required for the intramacrophage growth of *Francisella novicida*. Molecular Microbiology 29:247-259.

Birkbeck, T. H., M. Bordevik, M. K. Frøystad, and Å Baklien. 2007. Identification of *Francisella* sp. from atlantic salmon, *Salmo salar* L., in Chile. Journal of Fish Diseases 30: 505-507.

Bode E, Hurtle W, Norwood D (2004) Real-time PCR assay for a unique chromosomal sequence of *Bacillus anthracis*. J. Clin. Microbiol. 42:5825-5831

Brotcke, A., D. S. Weiss, C. C. Kim, P. Chain, S. Malfatti, E. Garcia, and D. M. Monack. 2006. Identification of Mg1A-regulated genes reveals novel virulence factors in *Francisella tularensis*. Infection and Immunity 74:6642-6655.

de Bruin, O. M., J. S. Ludu, and F. E. Nano. 2007. The *Francisella* pathogenicity island protein IglA localizes to the bacterial cytoplasm and is needed for intracellular growth. BMC Microbiology 7:1.

Chapman, F. A. 1992. Circular 1051, Department of Fisheries and Aquatic Sciences, Florida Cooperative Extension Service, Institute of Food and Agricultural Sciences, University of Florida.

Dennis, D. T., T. V. Inglesby, D. A. Henderson, J. G. Bartlett, M. S. Ascher, E. Eitzen, A. D. Fine, A. M. Friedlander, J. Hauer, M. Layton, S. R. Lillibridge, J. E. McDade, M. T. Osterholm, T. O'Toole, G. Parker, T. M. Perl, P. K. Russell, and K. Tonat. 2001. Tularemia as a biological weapon: medical and public health management. Journal of the American Medical Association 285:2763-2773.

Espy M J, Uhl J R, Sloan L M, Buckwalter S P, Jones M F, Vetter E A, Yao J D, Wengenack N L, Rosenblatt J E, Cockerill F R, III, Smith T F (2006) Real-time PCR in clinical microbiology: applications for routine laboratory testing. Clin. Microbiol. Rev. 19:165-256

Gallagher, L. A., E. Ramage, M. A. Jacobs, R. Kaul, M. Brittnacher, and C. Manoil. 2007. A comprehensive transposon mutant library of *Francisella novicida*, a bioweapon surrogate. Proceedings of the National Academy of Sciences of the United States of America 104:1009-1014.

Getchell R G, Groocock G H, Schumacher V L, Grimmett S G, Wooster G A, Bowser P R (2007) Quantitative polymerase chain reaction assay for largemouth bass virus. J. Aquat. Anim Health 19:226-233

Golovliov, I., M. Ericsson, G. Sandstrom, A. Tarnvik, and A. Sjostedt. 1997. Identification of proteins of *Francisella tularensis* induced during growth in macrophages and cloning of the gene encoding a prominently induced 23-kilodalton protein. Infection and Immunity 65:2183-2189.

Golovliov, I., V. Baranov, Z. Krocova, H. Kovarova, and A. Sjöstedt. 2003. An attenuated strain of the facultative intracellular bacterium *Francisella tularensis* can escape the phagosome of monocytic cells. Infection and Immunity 71: 5940-5950.

Grabowski L D, LaPatra S E, Cain K D. 2004. Systemic and mucosal antibody response in tilapia, *Oreochromis niloticus* (L.), following immunization with *Flavobacterium columnare*. J Fish Dis; 27(10):573-81

Griffin M J, Wise D J, Camus A C, Mauel M J, Greenway T E, Pote L M (2008) A real-time polymerase chain reaction assay for the detection of the myxozoan parasite *Henneguya ictaluri* in channel catfish. J. Vet. Diag. Invg. 20: Incomplete Hsieh, C. Y., M. C. Tung, C. Tu, C. D. Chang, and S. S. Tsai. 2006. Enzootics of visceral granulomas associated with *Francisella*-like organism infection in tilapia (*Oreochromis* spp.). Aquaculture 254:129-138.

Josupeit, H. 2008. Tilapia Market Report-April 2008. Food and Agriculture Organization of the United Nations (FAO). On line at: www.fao.org.

Kamaishi, T., Y. Fukuda, M. Nishiyama, H. Kawakami, T. Matsuyama, T. Yoshinaga, and N. Oseko. 2005. Identification and pathogenicity of intracellular *Francisella* bacterium in three-line grunt *Parapristipoma trilineatum*. Fish Pathology 40:67-71.

Kang, H. Y., J. Srinivasan, and R. Curtiss, III. 2002. Immune responses to recombinant pneumococcal PspA antigen delivered by live attenuated *Salmonella enterica* serovar Tymphimurium vaccine. Infection and Immunity. 70:1739-1749.

Keim, P., A. Johansson, and D. M. Wagner. 2007. Molecular epidemiology, evolution, and ecology of *Francisella*.

*Francisella tularensis*: Biology, Pathogenicity, Epidemiology, and Biodefense. Annals of the New York Academy of Sciences 1105:30-66.

Kidd L, Maggi R, Diniz P P V P, Hegarty B, Tucker M, Breitschwerdt E (2008). Evaluation of conventional and real-time PCR assays for detection and differentiation of spotted fever group *rickettsia* in dog blood. Veterinary Microbiology 193: 294-303

Kocagoz T, Saribas Z, Alp A (2005) Rapid determination of rifampin resistance in clinical isolates of *Mycobacterium tuberculosis* by real-time PCR. J. Clin. Microbiol. 43:6015-6019

Lai, X. H., I. Golovliov, and A. Sjostedt. 2004. Expression of IglC is necessary for intracellular growth and induction of apoptosis in murine macrophages by *Francisella tularensis*. Microbial Pathogenesis 37:225-230.

Lauriano, C. M., J. R. Barker, F. E. Nano, B. P. Arulanandam, and K. E. Klose. 2003. Allelic exchange in *Francisella tularensis* using PCR products. FEMS Microbiology Letters 229:195-202.

Lauriano, C. M., J. R. Barker, S. S. Yoon, F. E. Nano, B. P. Arulanandam, D. J. Hassett, and K. E. Klose. 2004. Mg1A regulates transcription of virulence factors necessary for *Francisella tularensis* intraamoebae and intramacrophage survival. Proceedings of the National Academy of Sciences 101:4246-4249.

Liu, J., X. Zogaj, J. R. Barker and K. E. Klose. 2007. Construction of targeted insertion mutations in *Francisella tularensis* subsp. *novicida*. BioTechniques 43:487-492.

Ludu, J. S., E. B. Nix, B. N. Duplantis, O. M. de Bruin, L. A. Gallagher, L. M. Hawley, and F. E. Nano. 2008-a. Genetic elements for selection, deletion mutagenesis and complementation in *Francisella* spp. FEMS Microbiology Letters 278:86-93.

Ludu, J. S., O. M. de Bruin, B. N. Duplantis, C. L. Schmerk, A. Y. Chou, K. L. Elkins, and F. E. Nano. 2008-b. The *Francisella* pathogenicity island protein PdpD is required for full virulence and associates with homologues of the type VI secretion system. Journal of Bacteriology 190: 4584-4595.

Maier, T. M., A. Havig, M. Casey, F. E. Nano, D. W. Frank, and T. C. Zahrt. 2004. Construction and characterization of a highly efficient *Francisella* shuttle plasmid. Applied and Environmental Microbiology 70:7511-7519.

Mauel, M. J., E. Soto, J. A. Morales, and J. Hawke. 2007. A Piscirickettsiosis-like Syndrome in Cultured Nile Tilapia in Latin America with *Francisella* spp. as the Pathogenic Agent. Journal of Aquatic Animal Health 19: 27-34.

Mikalsen, J., A. B. Olsen, T. Tengs, and D. J. Colquohoun. 2007. *Francisella philomiragia* subsp *noatunensis* subsp nov., isolated from farmed Atlantic cod (*Gadus morhua* L). International Journal of Systematic and Evolutionary Microbiology 57:1960-1965.

Mikalsen, J. and D. J. Colquohoun. 2009. *Francisella asiatica* sp. nov. isolated from farmed tilapia (*Oreochromis* sp.) and elevation of *Francisella philomiragia* subsp. *noatunensis* to species rank as *Francisella noatunensis* comb. nov., sp., nov. International Journal of Systematic and Evolutionary Microbiology. Epub ahead of print on 25 Sep. 2009.

Nano, F. E., N. Zhang, S. C. Cowley, K. E. Klose, K. K. Cheung, M. J. Roberts, J. S. Ludu, G. W. Letendre, A. I. Meierovics, G. Stephens, and K. L. Elkins. 2004. A *Francisella tularensis* pathogenicity island required for intramacrophage growth. Journal of Bacteriology 186:6430-6436.

Nano, F. E., and C. Schmerk. 2007. The *Francisella* pathogenicity island. Annals of the New York Academy of Sciences 1105:122-137.

Neumann N F, Barreda D, Belosevic M. 1998. Production of a macrophage growth factor(s) by a goldfish macrophage cell line and macrophages derived from goldfish kidney leukocytes. Dev Comp Immunol; 22(4):417-32

Ostland, V. E., J. A. Stannard, J. J. Creek, R. P. Hedrick, H. W. Ferguson, J. M. Carlberg, and M. E. Westerman. 2006. Aquatic *Francisella*-like bacterium associated with mortality of intensively cultured hybrid striped bass *Morone chrysops* x *M. saxatilis*. Diseases of Aquatic Organisms 72:135-145.

Ottem, K. F., A. Nylund, E. Karlsbakk, A. Friis-Moller, B. Krossoy, and D. Knappskog. 2007. New species in the genus *Francisella* (Gammaproteobacteria; Francisellaceae); *Francisella piscicida* sp. nov. isolated from cod (*Gadus morhua*). Archives of Microbiology 188:547-550.

Ottem K F, Nylund A, Isaksen T E, Karlsbakk E, Bergh O (2008) Occurrence of *Francisella piscicida* in farmed and wild Atlantic cod, *Gadus morhua* L., in Norway. J. Fish Dis. 31:525-534

Panangala V S, Shoemaker C A, Klesius P H (2007) TaqMan real-time polymerase chain reaction assay for rapid detection of *Flavobacteriuni columnare*. Aquaculture Research 38: 508-517

Reed L J, Muench H. 1938. A simple method of estimating fifty percent end points. Am J Hyg; (27):493-7.

Roberts, M. 1994. *Salmonella* as carriers of heterologous antigens, pp. 27-58; in O'Hagan (ed.), Novel Delivery Systems for Oral Diseases.

Santic, M., M. Molmeret, K. E. Klose, S. Jones, and Y. A. Kwaik. 2005. The *Francisella tularensis* pathogenicity island protein IglC and its regulator Mg1A are essential for modulating phagosome biogenesis and subsequent bacterial escape into the cytoplasm. Cell Microbiology 7:969-979.

Secombes C J. 1992. Isolation of salmonid macrophages and analysis of their killing activity. In: Stolen J S, Fletcher T C, Anderson D P, Robertson B S, van Muiswinkel W B, editors. Techniques in Fish Immunology, vol. 1. New Jersey: SOS Publications; 137-154

Shelby R A, Shoemaker C A, Klesius P H. 2002. Detection of Humoral Response to *Streptococcus iniae* Infection of Nile Tilapia, *Oreochromis niloticus*, by a Monoclonal Antibody-Based ELISA. J Appl Aquac; (12):23-31

Soto, E., J. Hawke, D. Fernandez, and J. A. Morales. 2009a. *Francisella* sp., an emerging pathogen of tilapia, *Oreochromis niloticus* (L.) in Costa Rica, Journal of Fish Disease, 32:713-722; epub. Jun. 8, 2009.

E. Soto et al., 2009b. Attenuation of the fish pathogen *Francisella* sp. by mutation of the iglC gene, Journal of Aquatic Animal Health, vol. 21, pp. 140-149, epub Oct. 12, 2009.

Soto, E., K. Bowles, D. Fernandez, and J. P. Hawke. 2010a. Development of a Real-time PER assay for identification and quantification of the fish pathogen *Francisella noatunensis* subsp. *Orientalis*," Diseases of Aquatic Organisms, vol. 89(3), pp. 199-207; epub Apr. 9, 2010.

E. Soto et al. 2010b. "Interaction of *Francsiella asiatica* with Tilapia (*Oreochromis niloticus*) innate immunity", Infection and Immunity, vol. 78, pp. 2070-2078; epub Feb. 16, 2010.

Sjostedt, A. 2007. Tularemia: history, epidemiology, pathogen physiology, and clinical manifestations. Annals of the New York Academy of Sciences 1105:1-29.

Suzuki K, Sakai D K (2007) Real-time PCR for quantification of viable *Renibacterium salmoninarum* in chum salmon *Oncorhynchus keta*. Dis. Aquat. Organ 74:209-223

Takahashi T, Tamura M, Takahashi S N, Matsumoto K, Sawada S, Yokoyama E, Nakayama T, Mizutani T, Takasu T, Nagase H (2007) Quantitative nested real-time PCR assay for assessing the clinical course of tuberculous meningitis. J. Neurol. Sci. 255:69-76

Tomaso H, Scholz H C, Neubauer H, Al D S, Seibold E, Landt O, Forsman M, Splettstoesser W D (2007) Real-time PCR using hybridization probes for the rapid and specific identification of *Francisella tularensis* subspecies *tularensis*. Mol. Cell Probes 21:12-16

Vonkavaara, M., M. V. Telepnev, P. Ryden, A. Sjostedt, and S. Stoven. 2008. *Drosophila melanogaster* as a model for elucidating the pathogenicity of *Francisella tularensis*. Cell Microbiolgy 10:1327-1338.

The complete disclosures of all references cited in this specification are hereby incorporated by reference. Also incorporated by reference is the complete disclosure of the following: (1) E. Soto et al., "Attenuation of the fish pathogen *Francisella* sp. by mutation of the iglC gene," Journal of Aquatic Animal Health, vol. 21, pp. 140-149 (2009), epub Oct. 12, 2009; (2) E. Soto et al., "*Francisella* sp., an emerging pathogen of tilapia, *Oreochromis niloticus* (L.) in Costa Rica," epub. Jun. 8, 2009, Journal of Fish Disease, vol. 32, pp. 713-722 (2009); (3) E. Soto et al., "Interaction of *Francsiella asiatica* with Tilapia (*Oreochromis niloticus*) innate immunity", Infection and Immunity, vol. 78, pp. 2070-2078; epub Feb. 16, 2010 (2010); (4) E. Soto et al., Development of a Real-time PCR assay for identification and quantification of the fish pathogen *Francisella noatunensis* subsp. *Orientalis*," Diseases of Aquatic Organisms, vol. 89(3), pp. 199-207; epub Apr. 9, 2010 (2010); and (5) E. Soto et al., In vitro and in vivo efficacy of florfenicol for treatment of *Francisella asiatica* infection in tilapia, Antimicrobial Agents and Chemotherapy, Aug. 16, 2010 (Epub ahead of print). In the event of an otherwise irreconcilable conflict, however, the present specification shall control.

What is claimed:

1. An attenuated Francisella bacterium isolated from fish comprising a mutant iglC gene, wherein said bacterium is selected from the group consisting of *Francisella asiatica* and *Francisella noatunensis.*

2. The attenuated bacterium as in claim 1, wherein the bacterium is *Francisella asiatica.*

3. The attenuated bacterium as in claim 1, wherein said mutant iglC gene has an insertion mutation of at least 100 base pairs as compared to the iglC gene of a wild-type *Francisella asiatica* bacterium.

4. The attenuated bacterium as in claim 1, wherein the attenuated bacterium is the attenuated *Francisella asiatica* bacterium with ATCC Accession Number PTA-11268.

5. A vaccine for protecting fish against a *Francisella* infection, comprising a protective amount of an attenuated *Francisella* bacterium as recited in claim 1.

6. A vaccine for protecting fish against a *Francisella* infection, comprising a protective amount of an attenuated *Francisella* bacterium as recited in claim 2.

7. A vaccine for protecting fish against a *Francisella* infection, comprising a protective amount of an attenuated *Francisella* bacterium as recited in claim 3.

8. A vaccine for protecting fish against a *Francisella* infection, comprising a protective amount of an attenuated *Francisella* bacterium as recited in claim 4.

9. The attenuated bacterium as in claim 1, wherein said attenuated bacterium additionally comprises an exogenous gene encoding an antigenic peptide or antigenic protein that is native to a fish pathogen other than *Francisella.*

10. The attenuated bacterium as in claim 1, wherein said attenuated bacterium additionally comprises an exogenous gene encoding a *Streptococcus* protein selected from the group consisting of surface immunogenic protein sipA, the cell surface associated protein cspA, and the components of the general protein secretion pathway secY.

11. A method of reducing the susceptibility of a fish to francisellosis, comprising administering to the fish a vaccine as recited in claim 5.

12. The method as in claim 11, wherein the fish is selected from the group consisting of tilapia, cod, three-line grunt, striped bass, hybrid striped bass, and salmon.

13. The method as in claim 11, wherein the fish is tilapia, striped bass, hybrid striped bass, and three line grunt.

14. The method as in claim 11, wherein the fish is tilapia.

15. The method as in claim 11, wherein said administering step comprises immersing the fish in said vaccine.

16. The method as in claim 11, wherein said administering step comprises feeding the fish a food product comprising said vaccine.

17. The method as in claim 11, wherein said administering step comprises injecting the fish with said vaccine intraperitoneally.

18. A method of reducing the susceptibility of fish selected from the group consisting of tilapia, three-line grunt, striped bass and hybrid striped bass to *Francisella asiatica*, comprising administering to the fish a vaccine as recited in claim 6.

19. The method as in claim 18, wherein the fish is tilapia.

20. The attenuated bacterium of claim 1, wherein the attenuated bacterium is *Francisella noatunensis.*

21. The attenuated bacterium of claim 20, wherein the attenuated bacterium is *Francisella noatunensis* subspecies *orientalis.*

* * * * *